(12) United States Patent
Lukyanov et al.

(10) Patent No.: US 7,157,565 B2
(45) Date of Patent: Jan. 2, 2007

(54) FAR RED SHIFTED FLUORESCENT PROTEINS

(75) Inventors: Sergey Lukyanov, Moscow (RU); Konstantin Lukyanov, Moscow (RU); Arcady Fradkov, Moscow (RU); Nadejda Gurskaya, Moscow (RU)

(73) Assignee: Clontech Laboratories, Inc., Mountain View, CA (US)

( * ) Notice: Subject to any disclaimer, the term of this patent is extended or adjusted under 35 U.S.C. 154(b) by 510 days.

(21) Appl. No.: 09/976,673

(22) Filed: Oct. 12, 2001

(65) Prior Publication Data

US 2002/0160473 A1 Oct. 31, 2002

Related U.S. Application Data

(60) Provisional application No. 60/240,018, filed on Oct. 12, 2000, provisional application No. 60/306,131, filed on Jul. 16, 2001.

(51) Int. Cl.
*C07H 21/01* (2006.01)
*C07K 1/00* (2006.01)
*C12P 21/06* (2006.01)

(52) U.S. Cl. ............ 536/23.1; 530/350; 435/69.1
(58) Field of Classification Search ............ 530/350; 536/23.1; 514/12; 435/69.1
See application file for complete search history.

(56) References Cited

U.S. PATENT DOCUMENTS

| 5,491,084 A | 2/1996 | Chalfie et al. |
| 5,874,304 A | 2/1999 | Zolotukhin et al. |
| 5,919,445 A | 7/1999 | Chao |
| 5,958,713 A | 9/1999 | Thastrup et al. |
| 5,968,738 A | 10/1999 | Anderson et al. |
| 5,968,750 A | 10/1999 | Zolotukhin et al. |
| 5,976,796 A | 11/1999 | Szalay et al. |
| 5,985,577 A | 11/1999 | Bulinski |
| 6,020,192 A | 2/2000 | Muzyczka et al. |
| 6,066,476 A | 5/2000 | Tsien et al. |
| 6,342,379 B1 * | 1/2002 | Tsien et al. .......... 435/173.4 |

FOREIGN PATENT DOCUMENTS

| DE | 197 18 | 5/1997 |
| WO | WO 99/49019 | 9/1999 |
| WO | WO 00/34318 | 12/1999 |
| WO | WO 00/34319 | 12/1999 |

(Continued)

OTHER PUBLICATIONS

Branden et al. "Introduction to Protein Structure", Garland Publishing Inc., New York, 1991, p. 247.*

(Continued)

*Primary Examiner*—Robert A. Wax
*Assistant Examiner*—Robert B. Mondesi
(74) *Attorney, Agent, or Firm*—Bret E. Field; Bozicevic, Field & Francis LLP

(57) ABSTRACT

Nucleic acid compositions encoding Stichodactylidaen chromoproteins and fluorescent mutants thereof. The proteins of interest are proteins that are colored and/or fluorescent, where this feature arises from the interaction of two or more residues of the protein. Also of interest are proteins that are substantially similar to, or mutants of, the above specific proteins, including non-aggregating mutants and mutants with modulated oligomerization characteristics as compared to wild type. Also provided are fragments of the nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

22 Claims, 19 Drawing Sheets

FOREIGN PATENT DOCUMENTS

Figure 3:
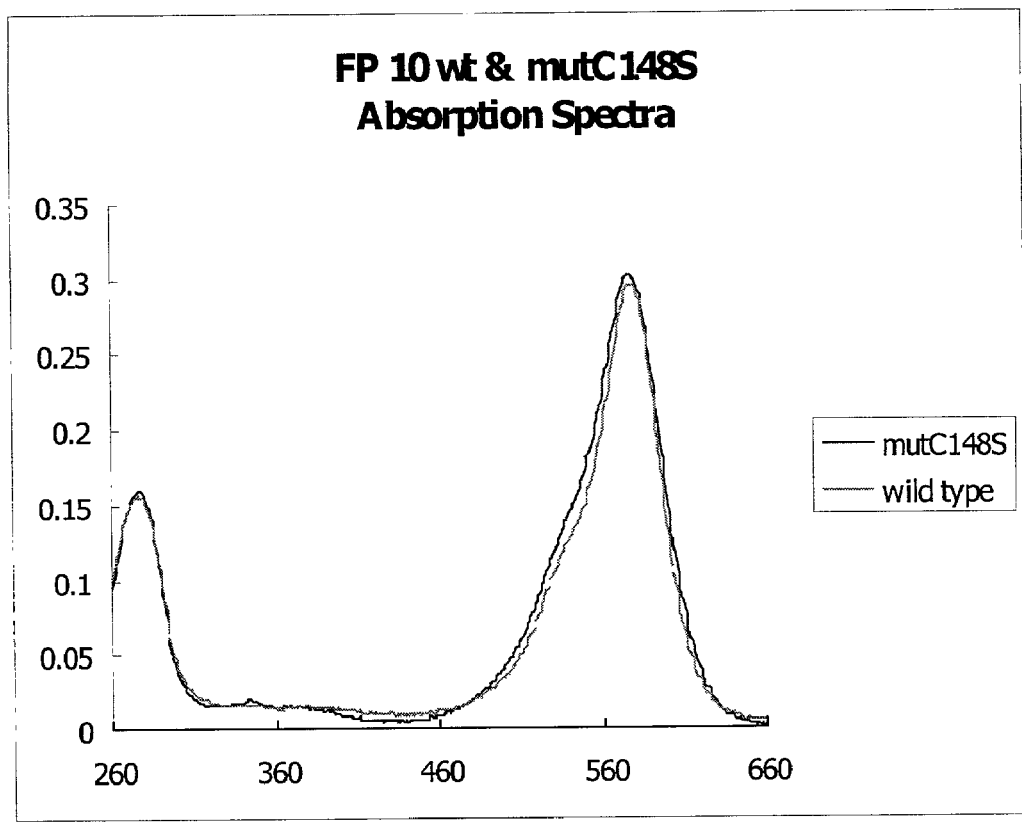

| WO | WO 00/34320 | 12/1999 |
| --- | --- | --- |
| WO | WO 00/34321 | 12/1999 |
| WO | WO 00/34322 | 12/1999 |
| WO | WO 00/34323 | 12/1999 |
| WO | WO 00/34324 | 12/1999 |
| WO | WO 00/34325 | 12/1999 |
| WO | WO 00/34326 | 12/1999 |
| WO | WO 00/34526 | 12/1999 |
| WO | WO 00/46233 | 8/2000 |
| WO | WO 01/27150 | 10/2000 |
| WO | WO 01/32688 | 5/2001 |
| WO | WO 01/34824 | 5/2001 |

OTHER PUBLICATIONS

Min et al., The emitting species dissociated from the enzyme can emit the light in Photinus pyralis luciferase system, Biochem Biophysics Tes Commun., Nov. 19, 1999;265(2):273-8.*

Heim et al., Wavelength mutations and posttranslational autoxidation of greeen fluoresecent protein (PNAS, vol. 91, pp. 12501-12504, 1994).*

Lukyanov et al., Natural animal coloration can be determined by a nonfluoresecent Green Fluorescent Protein homolog, Jun. 13, 2000, The Journal of Biological chemistry, vol. 275, No. 34, pp. 25879-25882.*

Rudinger J., Characteristics of amino acids as components of a peptide hormone sequence, University Park Press, 1994, pp. 1-7.*

Bowie et al., Deciphering the message in protein sequences: Tolerance to amino acid substitutions, Science, 1990, vol. 247, pp. 1306-1310.*

Wiedemann, et al., Cracks in the β-can: Fluorescent proteins from Anemonia sulcata (Anthozoa, Actinaria) Proc. Nat'l Acad. Sci. (Dec. 19, 2000) 97: 14091-14096.

Ehrig et al., "Green-Fluoresecnt Protein Mutants with Altered Fluorescence Excitation Spectra", FEBS Letters (1995) 367: 163-166.

Anderluh et al., Biochemical and Biophysical Research Communications (1996) 220:437-442.

Dove et al., Biological Bulletin (1995) 189:288-297.

Fradkov et al., FEBS Lett. (2000) 479(3):127-30.

Gurskaya et al., FEBS Lett. (2001) 507(1):16-20.

Gurskaya et al., BMC Biochem. (2001) 2:6.

Lukyanov, K., et al (2000) J Biol Chemistry 275(34):25879-25882.

Macek et al., Eur. J. Biochem. (1995) 234:329-335.

Martynov et al., J Biol Chem. (2001) 276:21012-6.

Matz, M.V., et al. (1999) *Nature Biotechnol.*, 17:969-973.

Terskikh et al., Science (2000) 290:1585-8.

Tsien, Annual Rev. of Biochemistry (1998) 67:509-544.

Tsien, Nat. Biotech. (1999) 17:956-957.

Ward et al., J. Biol. Chem. (1979) 254:781-788.

Wiedermann et al., Jarhrestagung der Deutschen Gesellschact furTropenokologie-gto. Ulm. 17-Feb. 19, 1999. Poster P-4.20.

Yarbrough et al., Proc Natl Acad Sci U S A (2001) 98:462-7.

\* cited by examiner

Figure 1

```
                10        20        30        40        50        60
5'ACCATTTGCTTTGGTTCCTTGGCAAACGAAAGTTTAGAACGAAAACTGACCCAAATTACA
                70        80        90       100       110       120
  TCTTCCTCCTGGATCCTTACCATGGCTGGTTTGTTGAAAGAAAGTATGCGCATCAAGATG
                                  M  A  G  L  L  K  E  S  M  R  I  K  M
               130       140       150       160       170       180
  TACATGGAAGGCACGGTTAATGGCCATTATTTCAAGTGTGAAGGAGAGGGAGACGGCAAC
  Y  M  E  G  T  V  N  G  H  Y  F  K  C  E  G  E  G  D  G  N
               190       200       210       220       230       240
  CCATTTACAGGTACGCAGAGCATGAGGATTCATGTCACCGAAGGGGCTCCATTACCATTT
  P  F  T  G  T  Q  S  M  R  I  H  V  T  E  G  A  P  L  P  F
               250       260       270       280       290       300
  GCCTTCGACATTTTGGCACCGTGTTGTGAGTACGGCAGCAGGACCTTTGTCCACCATACG
  A  F  D  I  L  A  P  C  C  E  Y  G  S  R  T  F  V  H  H  T
               310       320       330       340       350       360
  GCAGAGATTCCCGATTTCTTCAAGCAGTCTTTCCCTGAAGGCTTTACTTGGGAAAGAACC
  A  E  I  P  D  F  F  K  Q  S  F  P  E  G  F  T  W  E  R  T
               370       380       390       400       410       420
  ACAACCTATGAAGATGGAGGCATTCTTACTGCTCATCAGGACACAAGCCTGGAGGGGAAC
  T  T  Y  E  D  G  G  I  L  T  A  H  Q  D  T  S  L  E  G  N
               430       440       450       460       470       480
  TGCCTTATATACAAGGTGAAAGTCCTTGGTACCAATTTTCCTGCTGATGGCCCCGTGATG
  C  L  I  Y  K  V  K  V  L  G  T  N  F  P  A  D  G  P  V  M
               490       500       510       520       530       540
  AAGAACAAATCAGGAGGATGGGAGCCATGCACTGAGGTGGTTTATCCAGAGAATGGTGTC
  K  N  K  S  G  G  W  E  P  C  T  E  V  V  Y  P  E  N  G  V
               550       560       570       580       590       600
  CTGTGTGGACGTAATGTGATGGCCCTTAAAGTCGGTGATCGTCGTTTGATCTGCCATCTC
  L  C  G  R  N  V  M  A  L  K  V  G  D  R  R  L  I  C  H  L
               610       620       630       640       650       660
  TATACTTCTTACAGGTCCAAGAAAGCAGTCCGTGCCTTGACAATGCCAGGATTTCATTTT
  Y  T  S  Y  R  S  K  K  A  V  R  A  L  T  M  P  G  F  H  F
               670       680       690       700       710       720
  ACAGACATCCGCCTTCAGATGCCGAGGAAAAAGAAAGACGAGTACTTTGAACTGTACGAA
  T  D  I  R  L  Q  M  P  R  K  K  K  D  E  Y  F  E  L  Y  E
               730       740       750       760       770       780
  GCATCTGTGGCTAGGTACAGTGATCTTCCTGAAAAAGCAAATTGATTGTTCCCAGTGACA
  A  S  V  A  R  Y  S  D  L  P  E  K  A  N  *
               790       800       810       820       830       840
  CCAGACTGCTGTCAGCTTTTGGTTAAAGCCCGAAAGACAAAAGGACATTTGTAGTTTAGT
               850       860       870       880       890       900
  TTATATTTCCCTTTCATTTGTGAATCAACATTGTACTCTCTGTAAACCTTTAAAATGCTC
               910
  CATTAAACCT 3'  (SEQ ID NOs: 01 & 02)
```

Figure 2

```
            10         20         30         40         50         60
5'ACCATTTGCTTTGGTTCCTTGGCAAACGAAAGTTTAGACGAAAACTGACCCAAATTACAT 70         80         90        100        110        120
CCTCCTGATCCTTACCATGGCTGGTTTGTTGAAAGAAAGTATGCGCATCAAGATGTACAT
                    M   A   G   L   L   K   E   S   M   R   I   K   M   Y   M 130        140        150        160        170        180
GGAAGGCACGGTTAATGGCCATTATTTCAAGTGTGAAGGAGAGGGAGACGGCAACCCATT
  E   G   T   V   N   G   H   Y   F   K   C   E   G   E   G   D   G   N   P   F 190        200        210        220        230        240
TACAGGTACGCAGAGCATGAGGATTCATGTCACCGAAGGGGCTCCATTACCATTTGCCTT
  T   G   T   Q   S   M   R   I   H   V   T   E   G   A   P   L   P   F   A   F 250        260        270        280        290        300
CGACATTTTGGCACCGTGTTGTGAGTACGGCAGCAGGACCTTTGTCCACCATACGGCAGA
  D   I   L   A   P   C   C   E   Y   G   S   R   T   F   V   H   H   T   A   E 310        320        330        340        350        360
GATTCCCGATTTCTTCAAGCAGTCTTTCCCTGAAGGCTTTACTTGGGAAAGAACCACAAC
  I   P   D   F   F   K   Q   S   F   P   E   G   F   T   W   E   R   T   T   T 370        380        390        400        410        420
CTATGAAGATGGAGGCATTCTTACTGCTCATCAGGACACAAGCCTGGAGGGGAACTGCCT
  Y   E   D   G   G   I   L   T   A   H   Q   D   T   S   L   E   G   N   C   L 430        440        450        460        470        480
TATATACAAGGTGAAAGTCCTTGGTACCAATTTTCCTGCTGATGGCCCCGTGATGAAGAA
  I   Y   K   V   K   V   L   G   T   N   F   P   A   D   G   P   V   M   K   N 490        500        510        520        530        540
CAAATCAGAAGGATGGGAGCCATGCACTGAGGTGGTTTATCCAGATAATGGTGTCCTGTG
  K   S   E   G   W   E   P   C   T   E   V   V   Y   P   D   N   G   V   L   C 550        560        570        580        590        600
TGGACGTAATGTGATGGCCCTTAAAGTCGGTGATCGTCGTTTGATCTGCCATCTCTATAC
  G   R   N   V   M   A   L   K   V   G   D   R   R   L   I   C   H   L   Y   T 610        620        630        640        650        660
TTCTTACAGGTCCAAGAAAGCAGTCCGTGCCTTGACAATGCCAGGATTTCATTTTACAGA
  S   Y   R   S   K   K   A   V   R   A   L   T   M   P   G   F   H   F   T   D 670        680        690        700        710        720
CATCCGCCTTCAGATGCCGAGGAAAAAGAAAGACGAGTACTTTGAACTGTACGAAGCATC
  I   R   L   Q   M   P   R   K   K   D   E   Y   F   E   L   Y   E   A   S 730        740        750        760        770        780
TGTGGCTAGGTACAGTGATCTTCCTGAAAAAGCAAATTGATTGTTCCCAGTGACACCAGA
  V   A   R   Y   S   D   L   P   E   K   A   N   *

790        800        810        820        830        840
CTGCTGTCAGCTTTTGGTTAAAGCCCGAAAGACAAAAGGACATTTGTAGTTTTAGTTTAT 850        860        870        880        890        900
ATTTTCCCTTTCATTTTGTGAATCAACATTGTACTCTCTGTAAACCTTTAAAATGCTCCA

TTAAACCT 3'  (SEQ ID NOs: 03 & 04)
```

Figure 4

```
                              ATGGCTGGTTTGTTGAAAGAAAGTATGCGCATCAAGATG
                               M  A  G  L  L  K  E  S  M  R  I  K  M

TACATGGAAGGCACGGTTAATGGCCATTATTTCAAGTGTGAAGGAGAGGGAGACGGCAAC
 Y  M  E  G  T  V  N  G  H  Y  F  K  C  E  G  E  G  D  G  N

CCATTTACAGGTACGCAGAGCATGAGGATTCATGTCACCGAAGGGGCTCCATTACCATTT
 P  F  T  G  T  Q  S  M  R  I  H  V  T  E  G  A  P  L  P  F

GCCTTCGACATTTTGGCACCGTGTTGTGAGTACGGCAGCAGGACCTTTGTCCACCATACG
 A  F  D  I  L  A  P  C  C  E  Y  G  S  R  T  F  V  H  H  T

GCAGAGATTCCCGATTTCTTCAAGCAGTCTTTCCCTGAAGGCTTTACTTGGGAAAGAACC
 A  E  I  P  D  F  F  K  Q  S  F  P  E  G  F  T  W  E  R  T

ACAACCTATGAAGATGGAGGCATTCTTACTGCTCATCAGGACACAAGCCTGGAGGGGAAC
 T  T  Y  E  D  G  G  I  L  T  A  H  Q  D  T  S  L  E  G  N

TGCCTTATATACAAGGTGAAAGTCCTTGGTACCAATTTTCCTGCTGATGGCCCCGTGATG
 C  L  I  Y  K  V  K  V  L  G  T  N  F  P  A  D  G  P  V  M

AAGAACAAATCAGGAGGATGGGAGCCAAGCACTGAGGTGGTTTATCCAGAGAATGGTGTC
 K  N  K  S  G  G  W  E  P  S  T  E  V  V  Y  P  E  N  G  V

CTGTGTGGACGTAATGTGATGGCCCTTAAAGTCGGTGATCGTCGTTTGATCTGCCATCTC
 L  C  G  R  N  V  M  A  L  K  V  G  D  R  R  L  I  C  H  L

TATACTTCTTACAGGTCCAAGAAAGCAGTCCGTGCCTTGACAATGCCAGGATTTCATTTT
 Y  T  S  Y  R  S  K  K  A  V  R  A  L  T  M  P  G  F  H  F

ACAGACATCCGCCTTCAGATGCCGAGGAAAAAGAAAGACGAGTACTTTGAACTGTACGAA
 T  D  I  R  L  Q  M  P  R  K  K  K  D  E  Y  F  E  L  Y  E

GCATCTGTGGCTAGGTACAGTGATCTTCCTGAAAAAGCAAATTGA
 A  S  V  A  R  Y  S  D  L  P  E  K  A  N  *
(SEQ ID NOs: 05 & 06)
```

Figure 6

```
                  80         90        100        110        120
           ATGTCTGGTTTGTTGAAAGAAAGTATGCGCATCAAGATGTACAT
            M  S  G  L  L  K  E  S  M  R  I  K  M  Y  M 130        140        150        160        170        180
GGAAGGCACGGTTAATGGCCATTATTTCAAGTGTGAAGGAGAGGGAGACGGCAACCCATT
 E  G  T  V  N  G  H  Y  F  K  C  E  G  E  G  D  G  N  P  F 190        200        210        220        230        240
TGCAGGTACGCAGAGCATGAGGATTCATGTCACCGAAGGGGCTCCATTACCATTTGCCTT
 A  G  T  Q  S  M  R  I  H  V  T  E  G  A  P  L  P  F  A  F 250        260        270        280        290        300
CGACATTTTGGCACCGTGTTGTGAGTACGGCAGCAGGACCTTTGTCCACCATACGGCAGA
 D  I  L  A  P  C  C  E  Y  G  S  R  T  F  V  H  H  T  A  E 310        320        330        340        350        360
GATTCCCGATTTCTTCAAGCAGTCTTTCCCTGAAGGCTTTACTTGGGAAAGAACCACAAC
 I  P  D  F  F  K  Q  S  F  P  E  G  F  T  W  E  R  T  T  T 370        380        390        400        410        420
CTATGAAGATGGAGGCATTCTTACTGCTCATCAGGACACAAGCCTGGAGGGGAACTGCCT
 Y  E  D  G  G  I  L  T  A  H  Q  D  T  S  L  E  G  N  C  L 430        440        450        460        470        480
TATATACAAGGTGAAAGTCCTTGGTACCAATTTTCCTGCTGATGGCCCCGTGATGAAGAA
 I  Y  K  V  K  V  L  G  T  N  F  P  A  D  G  P  V  M  K  N 490        500        510        520        530        540
CAAATCAGGAGGATGGGAGCCAAGCACTGAGGTGGTTTATCCAGAGAATGGTGTCCTGTG
 K  S  G  G  W  E  P  S  T  E  V  V  Y  P  E  N  G  V  L  C 550        560        570        580        590        600
TGGACGTAATGTGATGGCCCTTAAAGTCGGTGATCGTCGTTTGATCTGCCATCACTATAC
 G  R  N  V  M  A  L  K  V  G  D  R  R  L  I  C  H  H  Y  T 610        620        630        640        650        660
TTCTTACAGGTCCAAGAAAGCAGTCCGTGCCTTGACAATGCCAGGATTTCATTTTACAGA
 S  Y  R  S  K  K  A  V  R  A  L  T  M  P  G  F  H  F  T  D 670        680        690        700        710        720
CATCCGCCTTCAGATGCTGAGGAAAGAGAAAGACGAGTACTTTGAACTGTACGAAGCATC
 I  R  L  Q  M  L  R  K  E  K  D  E  Y  F  E  L  Y  E  A  S 730        740        750        760
TGTGGCTAGGTACAGTGATCTTCCTGAAAAAGCAAATTGA
 V  A  R  Y  S  D  L  P  E  K  A  N  *    (SEQ ID NOs: 07 & 08)
```

Figure 8

```
                    ATGTCTGGTTTGTTGAAAGAAAGTATGCGCATCAAGATGTACAT
                    M   S   G   L   L   K   E   S   M   R   I   K   M   Y   M

GGAAGGCACGGTTAATGGCCATTATTTCAAGTGTGAAGGAGAGGGAGACGGCAACCCATT
E   G   T   V   N   G   H   Y   F   K   C   E   G   E   G   D   G   N   P   F

TGCAGGTACGCAGAGCATGAGGATTCATGTCACCGAAGGGGCTCCATTACCATTTGCCTT
A   G   T   Q   S   M   R   I   H   V   T   E   G   A   P   L   P   F   A   F

CGACATTTTGGCACCGTGTTGTGCGTACGGCAGCAGGACCTTTGTCCACCATACGGCAGA
D   I   L   A   P   C   C   A   Y   G   S   R   T   F   V   H   H   T   A   E

GATTCCCGATTTCTTCAAGCAGTCTTTCCCTGAAGGCTTTACTTGGGAAAGAACCACAAC
I   P   D   F   F   K   Q   S   F   P   E   G   F   T   W   E   R   T   T   T

CTATGAAGATGGAGGCATTCTTACTGCTCATCAGGACACAAGCCTGGAGGGGAACTGCCT
Y   E   D   G   G   I   L   T   A   H   Q   D   T   S   L   E   G   N   C   L
                                                    ←─────────────────────

TATATACAAGGTGAAAGTCCTTGGTACCAATTTTCCTGCTGATGGCCCCGTGATGAAGAA
I   Y   K   V   K   V   L   G   T   N   F   P   A   D   G   P   V   M   K   N

CAAATCAGGAGGATGGGAGCCAAGCACTGAGGTGGTTTATCCAGAGAATGGTGTCCTGTG
K   S   G   G   W   E   P   S   T   E   V   V   Y   P   E   N   G   V   L   C

TGGACGTAATGTGATGGCCCTTAAAGTCGGTGATCGTCGTTTGATCTGCCATCACTATAC
G   R   N   V   M   A   L   K   V   G   D   R   R   L   I   C   H   H   Y   T

TTCTTACAGGTCCAAGAAAGCAGTCCGTGCCTTGACAATGCCAGGATTTCATTTTACAGA
S   Y   R   S   K   K   A   V   R   A   L   T   M   P   G   F   H   F   T   D

CATCCGCCTTCAGATGCTGAGGAAAGAGAAAGACGAGTACTTTGAACTGTACGAAGCATC
I   R   L   Q   M   L   R   K   E   K   D   E   Y   F   E   L   Y   E   A   S

TGTGGCTAGGTACAGTGATCTTCCTGAAAAAGCAAATTGA
V   A   R   Y   S   D   L   P   E   K   A   N   *
```

(SEQ ID NO: 09 & 10)

Figure 10

A.

```
M S G L L K E S M R I K M Y M E G T V N G H Y
F K C E G E G D G N P F A G T Q S M R I H V T
E G A P L P F A F D I L A P C C E Y G S R T F
V H H T A E I P D F F K Q S F P E G F T W E R
T T T Y E D G G I L T A H Q D T S L E G N C L
I Y K V K V H G T N F P A D G P V M K N K S G
G W E P S T E V V Y P E N G V L C G R N V M A
L K V G D R H L I C H H Y T S Y R S K K A V R
A L T M P G F H F T D I R L Q M L R K K K D E
Y F E L Y E A S V A R Y S D L P E K A N        (SEQ ID
NO:12)
```

B.

ATGGTGAGCGGCCTGCTGAAGGAGAGTATGCGCATCAAGATGTACATGGAGGGCACCGTGAACGGCCAC

TACTTCAAGTGCGAGGGCGAGGGCGACGGCAACCCCTTCGCCGGCACCCAGAGCATGAGAATCCACGTG

ACCGAGGGCGCCCCCCTGCCCTTCGCCTTCGACATCCTGGCCCCCTGCTGCGAGTACGGCAGCAGGACC

TTCGTGCACCACACCGCCGAGATCCCCGACTTCTTCAAGCAGAGCTTCCCCGAGGGCTTCACCTGGGAG

AGAACCACCACCTACGAGGACGGCGGCATCCTGACCGCCCACCAGGACACCAGCCTGGAGGGCAACTGC

CTGATCTACAAGGTGAAGGTGCACGGCACCAACTTCCCCGCCGACGGCCCCGTGATGAAGAACAAGAGC

GGCGGCTGGGAGCCCAGCACCGAGGTGGTGTACCCCGAGAACGGCGTGCTGTGCGGCCGGAACGTGATG

GCCCTGAAGGTGGGCGACCGGCACCTGATCTGCCACCACTACACCAGCTACCGGAGCAAGAAGGCCGTG

CGCGCCCTGACCATGCCCGGCTTCCACTTCACCGACATCCGGCTCCAGATGCTGCGGAAGAAGAAGGAC

GAGTACTTCGAGCTGTACGAGGCCAGCGTGGCCCGGTACAGCGACCTGCCCGAGAAGGCCAACTGA (SEQ ID NO:11)

C.

MSGLLKESMRIKMYMEGTVNGHYFKCEGEGDGNPFAGTQSMRIHVTEGAPLPFAFDILAPCCEYGSRTF
VHHTAEIPDFFKQSFPEGFTWERTTTYEDGGILTAHQDTSLEGNCLIYKVKVHGTNFPADGPVMKNKSG
GWEPSTEVVYPENGVLCGRNVMALKVGDRRLICHHYTSYRSKKAVRALTMPGFHFTDIRLQMLRKEKDE
YFELYEASVARYSDLPEKAN*   SEQ ID NO:14)

D.

ATGGTGAGCGGCCTGCTGAAGGAGAGCATGCGCATCAAGATGTACATGGAGGGCACCGTGAACGGCCAC
TACTTCAAGTGCGAGGGCGAGGGCGACGGCAACCCCTTCGCCGGCACCCAGAGCATGCGGATCCACGTG
ACCGAGGGCGCCCCCCTGCCCTTCGCCTTCGACATCCTGGCCCCCTGCTGCGAGTACGGCAGCAGGACC
TTCGTGCACCACACCGCCGAGATCCCCGACTTCTTCAAGCAGAGCTTCCCCGAGGGCTTCACCTGGGAG
AGAACCACCACCTACGAGGACGGCGGCATCCTGACCGCCCACCAGGACACCAGCCTGGAGGGCAACTGC
CTGATCTACAAGGTGAAGGTGCTGGGCACCAACTTCCCCGCCGACGGCCCCGTGATGAAGAACAAGAGC
GGCGGCTGGGAGCCCAGCACCGAGGTGGTGTACCCCGAGAACGGCGTGCTGTGCGGCCGGAACGTGATG
GCCCTGAAGGTGGGCGACCGGCGGCTGATCTGCCACCACTACACCAGCTACCGGAGCAAGAAGGCCGTG
CGGGCCCTGACCATGCCCGGCTTCCACTTCACCGACATCCGGCTGCAGATGCTGCGGAAGGAGAAGGAC
GAGTACTTCGAGCTGTACGAGGCCAGCGTGGCCCGGTACAGCGACCTGCCCGAGAAGGCCAACTGA
(SEQ ID NO:13)

FIGURE 12

```
  1    A CCG GTC GCC ACC ATG GTG AGC GGC CTG CTG AAG GAG AGC ATG CGC    46
  1        AgeI        M   V   S   G   L   L   K   E   S   M   R       11

47    ATC AAG ATG TAC ATG GAG GGC ACC GTG AAC GGC CAC TAC TTC AAG TGC    94
 12     I   K   M   Y   M   E   G   T   V   N   G   H   Y   F   K   C    27

95    GAG GGC GAG GGC GAC GGC AAC CCC TTC GCC GGC ACC CAG AGC ATG CGG   142
 28     E   G   E   G   D   G   N   P   F   A   G   T   Q   S   M   R    43

143    ATC CAC GTG ACC GAG GGC GCC CCC CTG CCC TTC GCC TTC GAC ATC CTG   190
 44     I   H   V   T   E   G   A   P   L   P   F   A   F   D   I   L    59

191    GCC CCC TGC TGC GAG TAC GGC AGC AGG ACC TTC GTG CAC CAC ACC GCC   238
 60     A   P   C   C   E   Y   G   S   R   T   F   V   H   H   T   A    75

239    GAG ATC CCC GAC TTC TTC AAG CAG AGC TTC CCC GAG GGC TTC ACC TGG   286
 76     E   I   P   D   F   F   K   Q   S   F   P   E   G   F   T   W    91

287    GAG AGA ACC ACC ACC TAC GAG GAC GGC GGC ATC CTG ACC GCC CAC CAG   334
 92     E   R   T   T   T   Y   E   D   G   G   I   L   T   A   H   Q   107

335    GAC ACC AGC CTG GAG GGC AAC TGC CTG ATC TAC AAG GTG AAG GTG CTG   382
108     D   T   S   L   E   G   N   C   L   I   Y   K   V   K   V   L   123

383    GGC ACC AAC TTC CCC GCC GAC GGC CCC GTG ATG AAG AAC AAG AGC GGC   430
124     G   T   N   F   P   A   D   G   P   V   M   K   N   K   S   G   139

431    GGC TGG GAG CCC AGC ACC GAG GTG GTG TAC CCC GAG AAC GGC GTG CTG   478
140     G   W   E   P   S   T   E   V   V   Y   P   E   N   G   V   L   155

479    TGC GGC CGG AAC GTG ATG GCC CTG AAG GTG GGC GAC CGG CGG CTG ATC   526
156     C   G   R   N   V   M   A   L   K   V   G   D   R   R   L   I   171

527    TGC CAC CAC TAC ACC AGC TAC CGG AGC AAG AAG GCC GTG CGG GCC CTG   574
172     C   H   H   Y   T   S   Y   R   S   K   K   A   V   R   A   L   187

575    ACC ATG CCC GGC TTC CAC TTC ACC GAC ATC CGG CTG CAG ATG CTG CGG   622
188     T   M   P   G   F   H   F   T   D   I   R   L   Q   M   L   R   203

623    AAG GAG AAG GAC GAG TAC TTC GAG CTG TAC GAG GCC AGC GTG GCC CGG   670
204     K   E   K   D   E   Y   F   E   L   Y   E   A   S   V   A   R   219

671    TAC AGC GAC CTG CCC GAG AAG GCC AAC AGA TCT CCC GGG ATG GTG AGC   718
220     Y   S   D   L   P   E   K   A   N   R   S   P   G   M   V   S   235

719    GGC CTG CTG AAG GAG AGC ATG CGC ATC AAG ATG TAC ATG GAG GGC ACC   766
236     G   L   L   K   E   S   M   R   I   K   M   Y   M   E   G   T   251

767    GTG AAC GGC CAC TAC TTC AAG TGC GAG GGC GAG GGC GAC GGC AAC CCC   814
252     V   N   G   H   Y   F   K   C   E   G   E   G   D   G   N   P   267

815    TTC GCC GGC ACC CAG AGC ATG CGG ATC CAC GTG ACC GAG GGC GCC CCC   862
268     F   A   G   T   Q   S   M   R   I   H   V   T   E   G   A   P   283

863    CTG CCC TTC GCC TTC GAC ATC CTG GCC CCC TGC TGC GAG TAC GGC AGC   910
284     L   P   F   A   F   D   I   L   A   P   C   C   E   Y   G   S   299
```

```
Figure 12 (continued)
 911  AGG ACC TTC GTG CAC CAC ACC GCC GAG ATC CCC GAC TTC TTC AAG CAG   958
 300   R   T   F   V   H   H   T   A   E   I   P   D   F   F   K   Q   315

959  AGC TTC CCC GAG GGC TTC ACC TGG GAG AGA ACC ACC ACC TAC GAG GAC  1006
 316   S   F   P   E   G   F   T   W   E   R   T   T   T   Y   E   D   331

1007  GGC GGC ATC CTG ACC GCC CAC CAG GAC ACC AGC CTG GAG GGC AAC TGC  1054
 332   G   G   I   L   T   A   H   Q   D   T   S   L   E   G   N   C   347

1055  CTG ATC TAC AAG GTG AAG GTG CTG GGC ACC AAC TTC CCC GCC GAC GGC  1102
 348   L   I   Y   K   V   K   V   L   G   T   N   F   P   A   D   G   363

1103  CCC GTG ATG AAG AAC AAG AGC GGC GGC TGG GAG CCC AGC ACC GAG GTG  1150
 364   P   V   M   K   N   K   S   G   G   W   E   P   S   T   E   V   379

1151  GTG TAC CCC GAG AAC GGC GTG CTG TGC GGC CGG AAC GTG ATG GCC CTG  1198
 380   V   Y   P   E   N   G   V   L   C   G   R   N   V   M   A   L   395

1199  AAG GTG GGC GAC CGG CGG CTG ATC TGC CAC CAC TAC ACC AGC TAC CGG  1246
 396   K   V   G   D   R   R   L   I   C   H   H   Y   T   S   Y   R   411

1247  AGC AAG AAG GCC GTG CGG GCC CTG ACC ATG CCC GGC TTC CAC TTC ACC  1294
 412   S   K   K   A   V   R   A   L   T   M   P   G   F   H   F   T   427

1295  GAC ATC CGG CTG CAG ATG CTG CGG AAG GAG AAG GAC GAG TAC TTC GAG  1342
 428   D   I   R   L   Q   M   L   R   K   E   K   D   E   Y   F   E   443

1343  CTG TAC GAG GCC AGC GTG GCC CGG TAC AGC GAC CTG CCC GAG AAG GCC  1390
 444   L   Y   E   A   S   V   A   R   Y   S   D   L   P   E   K   A   459

1391  AAC TGA
 460   N   *

(SEQ ID NOS. 15 & 16)
```

Figure 13

| | | | | | | | | | | | | | | | | |
|---|---|---|---|---|---|---|---|---|---|---|---|---|---|---|---|---|
| 1 | A | CCG GTC | GCC | ACC | ATG | GTG | AGC | GGC | CTG | CTG | AAG | GAG | AGC | ATG | CGC | 46 |
| 1 | | AgeI | | | M | V | S | G | L | L | K | E | S | M | R | 11 |
| 47 | ATC | AAG | ATG | TAC | ATG | GAG | GGC | ACC | GTG | AAC | GGC | CAC | TAC | TTC | AAG | TGC | 94 |
| 12 | I | K | M | Y | M | E | G | T | V | N | G | H | Y | F | K | C | 27 |
| 95 | GAG | GGC | GAG | GGC | GAC | GGC | AAC | CCC | TTC | GCC | GGC | ACC | CAG | AGC | ATG | CGG | 142 |
| 28 | E | G | E | G | D | G | N | P | F | A | G | T | Q | S | M | R | 43 |
| 143 | ATC | CAC | GTG | ACC | GAG | GGC | GCC | CCC | CTG | CCC | TTC | GCC | TTC | GAC | ATC | CTG | 190 |
| 44 | I | H | V | T | E | G | A | P | L | P | F | A | F | D | I | L | 59 |
| 191 | GCC | CCC | TGC | TGC | GAG | TAC | GGC | AGC | AGG | ACC | TTC | GTG | CAC | CAC | ACC | GCC | 238 |
| 60 | A | P | C | C | E | Y | G | S | R | T | F | V | H | H | T | A | 75 |
| 239 | GAG | ATC | CCC | GAC | TTC | TTC | AAG | CAG | AGC | TTC | CCC | GAG | GGC | TTC | ACC | TGG | 286 |
| 76 | E | I | P | D | F | F | K | Q | S | F | P | E | G | F | T | W | 91 |
| 287 | GAG | AGA | ACC | ACC | ACC | TAC | GAG | GAC | GGC | GGC | ATC | CTG | ACC | GCC | CAC | CAG | 334 |
| 92 | E | R | T | T | T | Y | E | D | G | G | I | L | T | A | H | Q | 107 |
| 335 | GAC | ACC | AGC | CTG | GAG | GGC | AAC | TGC | CTG | ATC | TAC | AAG | GTG | AAG | GTG | CTG | 382 |
| 108 | D | T | S | L | E | G | N | C | L | I | Y | K | V | K | V | L | 123 |
| 383 | GGC | ACC | AAC | TTC | CCC | GCC | GAC | GGC | CCC | GTG | ATG | AAG | AAC | AAG | AGC | GGC | 430 |
| 124 | G | T | N | F | P | A | D | G | P | V | M | K | N | K | S | G | 139 |
| 431 | GGC | TGG | GAG | CCC | AGC | ACC | GAG | GTG | GTG | TAC | CCC | GAG | AAC | GGC | GTG | CTG | 478 |
| 140 | G | W | E | P | S | T | E | V | V | Y | P | E | N | G | V | L | 155 |
| 479 | TGC | GGC | CGG | AAC | GTG | ATG | GCC | CTG | AAG | GTG | GGC | GAC | CGG | CGG | CTG | ATC | 526 |
| 156 | C | G | R | N | V | M | A | L | K | V | G | D | R | R | L | I | 171 |
| 527 | TGC | CAC | CAC | TAC | ACC | AGC | TAC | CGG | AGC | AAG | AAG | GCC | GTG | CGG | GCC | CTG | 574 |
| 172 | C | H | H | Y | T | S | Y | R | S | K | K | A | V | R | A | L | 187 |
| 575 | ACC | ATG | CCC | GGC | TTC | CAC | TTC | ACC | GAC | ATC | CGG | CTG | CAG | ATG | CTG | CGG | 622 |
| 188 | T | M | P | G | F | H | F | T | D | I | R | L | Q | M | L | R | 203 |
| 623 | AAG | GAG | AAG | GAC | GAG | TAC | TTC | GAG | CTG | TAC | GAG | GCC | AGC | GTG | GCC | CGG | 670 |
| 204 | K | E | K | D | E | Y | F | E | L | Y | E | A | S | V | A | R | 219 |
| 671 | TAC | AGC | GAC | CTG | CCC | GAG | AAG | GCC | AAC | AGA TCT | CCC GGG | ATG | GTG | AGC | 718 |
| 220 | Y | S | D | L | P | E | K | A | N | R S | P G | M | V | S | 235 |
| 719 | GGC | CTG | CTG | AAG | GAG | AGC | ATG | CGC | ATC | AAG | ATG | TAC | ATG | GAG | GGC | ACC | 766 |
| 236 | G | L | L | K | E | S | M | R | I | K | M | Y | M | E | G | T | 251 |
| 767 | GTG | AAC | GGC | CAC | TAC | TTC | AAG | TGC | GAG | GGC | GAG | GGC | GAC | GGC | AAC | CCC | 814 |
| 252 | V | N | G | H | Y | F | K | C | E | G | E | G | D | G | N | P | 267 |
| 815 | TTC | GCC | GGC | ACC | CAG | AGC | ATG | CGG | ATC | CAC | GTG | ACC | GAG | GGC | GCC | CCC | 862 |
| 268 | F | A | G | T | Q | S | M | R | I | H | V | T | E | G | A | P | 283 |

Figure 13 (continued)

```
 863 CTG CCC TTC GCC TTC GAC ATC CTG GCC CCC TGC TGC GAG TAC GGC AGC  910
 284  L   P   F   A   F   D   I   L   A   P   C   C   E   Y   G   S   299

911 AGG ACC TTC GTG CAC CAC ACC GCC GAG ATC CCC GAC TTC TTC AAG CAG  958
 300  R   T   F   V   H   H   T   A   E   I   P   D   F   F   K   Q   315

959 AGC TTC CCC GAG GGC TTC ACC TGG GAG AGA ACC ACC ACC TAC GAG GAC 1006
 316  S   F   P   E   G   F   T   W   E   R   T   T   T   Y   E   D   331

1007 GGC GGC ATC CTG ACC GCC CAC CAG GAC ACC AGC CTG GAG GGC AAC TGC 1054
 332  G   G   I   L   T   A   H   Q   D   T   S   L   E   G   N   C   347

1055 CTG ATC TAC AAG GTG AAG GTG CTG GGC ACC AAC TTC CCC GCC GAC GGC 1102
 348  L   I   Y   K   V   K   V   L   G   T   N   F   P   A   D   G   363

1103 CCC GTG ATG AAG AAC AAG AGC GGC GGC TGG GAG CCC AGC ACC GAG GTG 1150
 364  P   V   M   K   N   K   S   G   G   W   E   P   S   T   E   V   379

1151 GTG TAC CCC GAG AAC GGC GTG CTG TGC GGC CGG AAC GTG ATG GCC CTG 1198
 380  V   Y   P   E   N   G   V   L   C   G   R   N   V   M   A   L   395

1199 AAG GTG GGC GAC CGG CGG CTG ATC TGC CAC CAC TAC ACC AGC TAC CGG 1246
 396  K   V   G   D   R   R   L   I   C   H   H   Y   T   S   Y   R   411

1247 AGC AAG AAG GCC GTG CGG GCC CTG ACC ATG CCC GGC TTC CAC TTC ACC 1294
 412  S   K   K   A   V   R   A   L   T   M   P   G   F   H   F   T   427

1295 GAC ATC CGG CTG CAG ATG CTG CGG AAG GAG AAG GAC GAG TAC TTC GAG 1342
 428  D   I   R   L   Q   M   L   R   K   E   K   D   E   Y   F   E   443

1343 CTG TAC GAG GCC AGC GTG GCC CGG TAC AGC GAC CTG CCC GAG AAG GCC 1390
 444  L   Y   E   A   S   V   A   R   Y   S   D   L   P   E   K   A   459

1391 AAC AGA ACT CGA GCT ATG GAT GAT GAT ATC GCC G...                 1424
 460  N   R   T   R   A   M   D   D   D   I   A...                   470
                                   actin
(SEQ ID NOs. 17 & 18).
```

Figure 15

```
                    ATGGCTGGTTTGTTGAAAGAAAGTATGCGCATCAAGATGTACAT
                     M  A  G  L  L  K  E  S  M  R  I  K  M  Y  M

GGAAGGCACGGTTAATGGCCATTATTTCAAGTGTGAAGGAGAGGGAGACGGCAACCCATT
 E  G  T  V  N  G  H  Y  F  K  C  E  G  E  G  D  G  N  P  F

TACAGGTACGCAGAGCATGAGGATTCATGTCACCGAAGGGGCTCCATTACCATTTGCCTT
 T  G  T  Q  S  M  R  I  H  V  T  E  G  A  P  L  P  F  A  F

CGACATTTTGGCACCGTGTTGTGAGTACGGCAGCAGGACCTTTGTCCACCATACGGCAGA
 D  I  L  A  P  C  C  E  Y  G  S  R  T  F  V  H  H  T  A  E

GATTCCCGATTTCTTCAAGCAGTCTTTCCCTGAAGGCTTTACTTGGGAAAGAACCACAAC
 I  P  D  F  F  K  Q  S  F  P  E  G  F  T  W  E  R  T  T  T

CTATGAAGATGGAGGCATTCTTACTGCTCATCAGGACACAAGCCTGGAGGGGAACTGCCT
 Y  E  D  G  G  I  L  T  A  H  Q  D  T  S  L  E  G  N  C  L

TATATACAAGGTGAAAGTCCTTGGTACCAATTTTCCTGCTGATGGCCCCGTGATGAAGAA
 I  Y  K  V  K  V  L  G  T  N  F  P  A  D  G  P  V  M  K  N

CAAATCAGGAGGATGGGAGCCAAGCACTGAGGTGGTTTATCCAGAGAATGGTGTCCTGTG
 K  S  G  G  W  E  P  S  T  E  V  V  Y  P  E  N  G  V  L  C

TGGACGTAATGTGATGGCCCTTAAAGTCGGTGATCGTCGTTTGATCTGCCATCTCTATAC
 G  R  N  V  M  A  L  K  V  G  D  R  R  L  I  C  H  L  Y  T

TTCTTACAGGTCCAAGAAAGCAGTCCGTGCCTTGACAATGCCAGGATTTCATTTTACAGA
 S  Y  R  S  K  K  A  V  R  A  L  T  M  P  G  F  H  F  T  D

CATCCGCCTTCAGATGCCGAGGAAAAAGAAAGACGAGTACTTTGAACTGTACGAAGCATC
 I  R  L  Q  M  P  R  K  K  D  E  Y  F  E  L  Y  E  A  S

TGTGGCTAGGTACAGTGATCTTCCTGAAAAAGCAAATTGA
 V  A  R  Y  S  D  L  P  E  K  A  N  *
SEQ ID NO:23 & 24
```

Figure 16

```
                        ATGTCTGGTTTGTTGAAAGAAAGTATGCGCATCAAGATGTACAT
                        M   S   G   L   L   K   E   S   M   R   I   K   M   Y   M

GGAAGGCACGGTTAATGGCCATTATTTCAAGTGTGAAGGAGAGGGAGACGGCAACCCATT
E   G   T   V   N   G   H   Y   F   K   C   E   G   E   G   D   G   N   P   F

TGCAGGTACGCAGAGCATGAGGATTCATGTCACCGAAGGGGCTCCATTACCATTTGCCTT
A   G   T   Q   S   M   R   I   H   V   T   E   G   A   P   L   P   F   A   F

CGACATTTTGGCACCGTGTTGTGCGTACGGCAGCAGGACCTTTGTCCACCATACGGCAGA
D   I   L   A   P   C   C   A   Y   G   S   R   T   F   V   H   H   T   A   E

GATTCCCGATTTCTTCAAGCAGTCTTTCCCTGAAGGCTTTACTTGGGAAAGAACCACAAC
I   P   D   F   F   K   Q   S   F   P   E   G   F   T   W   E   R   T   T   T

CTATGAAGATGGAGGCATTCTTACTGCTCATCAGGACACAAGCCTGGAGGGGAACTGCCT
Y   E   D   G   G   I   L   T   A   H   Q   D   T   S   L   E   G   N   C   L
                                ←─────────────

TATATACAAGGTGAAAGTCCTTGGTACCAATTTTCCTGCTGATGGCCCCGTGATGAAGAA
I   Y   K   V   K   V   L   G   T   N   F   P   A   D   G   P   V   M   K   N

CAAATCAGGAGGATGGGAGCCAAGCACTGAGGTGGTTTATCCAGAGAATGGTGTCCTGTG
K   S   G   G   W   E   P   S   T   E   V   V   Y   P   E   N   G   V   L   C

TGGACGTAATGTGATGGCCCTTAAAGTCGGTGATCGTCGTTTGATCTGCCATCACTATAC
G   R   N   V   M   A   L   K   V   G   D   R   R   L   I   C   H   H   Y   T

TTCTTACAGGTCCAAGAAAGCAGTCCGTGCCTTGACAATGCCAGGATTTCATTTTACAGA
S   Y   R   S   K   K   A   V   R   A   L   T   M   P   G   F   H   F   T   D

CATCCGCCTTCAGATGCTGAGGAAAAAGAAAGACGAGTACTTTGAACTGTACGAAGCATC
I   R   L   Q   M   L   R   K   K   D   E   Y   F   E   L   Y   E   A   S

TGTGGCTAGGTACAGTGATCTTCCTGAAAAAGCAAATTGA
V   A   R   Y   S   D   L   P   E   K   A   N   *
SEQ ID NO:25 & 26
```

Figure 17

```
              10         20         30         40         50         60
5'ACCATTTGCTTTGGTTCCTTGGCAAACGAAAGTTTAGAACGAAAACTGACCCAAATTACA
              70         80         90        100        110        120
  TCTTCCTCCTGGATCCTTACCATGGCTGGTTTGTTGAAAGAAAGTATGCGCATCAAGATG
                          M   A   G   L   L   K   E   S   M   R   I   K   M
             130        140        150        160        170        180
  TACATGGAAGGCACGGTTAATGGCCATTATTTCAAGTGTGAAGGAGAGGGAGACGGCAAC
  Y   M   E   G   T   V   N   G   H   Y   F   K   C   E   G   E   G   D   G   N
             190        200        210        220        230        240
  CCATTTACAGGTACGCAGAGCATGAGGATTCATGTCACCGAAGGGGCTCCATTACCATTT
  P   F   T   G   T   Q   S   M   R   I   H   V   T   E   G   A   P   L   P   F
             250        260        270        280        290        300
  GCCTTCGACATTTTGGCACCGTGTTGTGAGTACGGCAGCAGGACCTTTGTCCACCATACG
  A   F   D   I   L   A   P   C   C   E   Y   G   S   R   T   F   V   H   H   T
             310        320        330        340        350        360
  GCAGAGATTCCCGATTTCTTCAAGCAGTCTTTCCCTGAAGGCTTTACTTGGGAAAGAACC
  A   E   I   P   D   F   F   K   Q   S   F   P   E   G   F   T   W   E   R   T
             370        380        390        400        410        420
  ACAACCTATGAAGATGGAGGCATTCTTACTGCTCATCAGGACACAAGCCTGGAGGGGAAC
  T   T   Y   E   D   G   G   I   L   T   A   H   Q   D   T   S   L   E   G   N
             430        440        450        460        470        480
  TGCCTTATATACAAGGTGAAAGTCCTTGGTACCAATTTTCCTGCTGATGGCCCCGTGATG
  C   L   I   Y   K   V   K   V   L   G   T   N   F   P   A   D   G   P   V   M
             490        500        510        520        530        540
  AAGAACAAATCAGGAGGATGGGAGCCATGCACTGAGGTGGTTTATCCAGAGAATGGTGTC
  K   N   K   S   G   G   W   E   P   C   T   E   V   V   Y   P   E   N   G   V
             550        560        570        580        590        600
  CTGTGTGGACGTAATGTGATGGCCCTTAAAGTCGGTGATCGTCGTTTGATCTGCCATCTC
  L   C   G   R   N   V   M   A   L   K   V   G   D   R   R   L   I   C   H   L
             610        620        630        640        650        660
  TATACTTCTTACAGGTCCAAGAAAGCAGTCCGTGCCTTGACAATGCCAGGATTTCATTTT
  Y   T   S   Y   R   S   K   K   A   V   R   A   L   T   M   P   G   F   H   F
             670        680        690        700        710        720
  ACAGACATCCGCCTTCAGATGCCGAGGAAAACGAAAGACGAGTACTTTGAACTGTACGAA
  T   D   I   R   L   Q   M   P   R   K   T   K   D   E   Y   F   E   L   Y   E
             730        740        750        760        770        780
  GCATCTGTGGCTAGGTACAGTGATCTTCCTGAAAAAGCAAATTGATTGTTCCCAGTGACA
  A   S   V   A   R   Y   S   D   L   P   E   K   A   N   *
             790        800        810        820        830        840
  CCAGACTGCTGTCAGCTTTTGGTTAAAGCCCGAAAGACAAAAGGACATTTGTAGTTTAGT
             850        860        870        880        890        900
  TTATATTTCCCTTTCATTTGTGAATCAACATTGTACTCTCTGTAAACCTTTAAAATGCTC
             910
  CATTAAACCT 3' (SEQ ID NOs: 27 & 28)
```

FAR RED SHIFTED FLUORESCENT PROTEINS

CROSS REFERENCE TO RELATED APPLICATIONS

Pursuant to 35 U.S.C. §119(e), this application claims priority to the filing date of U.S. Provisional Patent Application Ser. No. 60/240,018 filed Oct. 12, 2000; and to the filing date of U.S. patent application Ser. No. 60/306,131 filed Jul. 16, 2001; the disclosures of which applications are herein incorporated by reference.

INTRODUCTION

Labeling is a tool for marking a protein, cell, or organism of interest and plays a prominent role in many biochemistry, molecular biology and medical diagnostic applications. A variety of different labels have been developed, including radiolabels, chromolabels, fluorescent labels, chemiluminescent labels, etc. However, there is continued interest in the development of new labels. Of particular interest is the development of new protein labels, including chromo- and/or fluorescent protein labels.

SUMMARY OF THE INVENTION

Nucleic acid compositions encoding far red shifted proteins, including fluorescent mutants Stichodactylidaen chromoproteins, as well as the polypeptide compositions encoded by the same, are provided. The proteins of interest are proteins that are colored and/or fluorescent, where this feature arises from the interaction of two or more residues of the protein. Also of interest are proteins that are substantially similar to, or mutants of, the above specific proteins, including non-aggregating mutants and mutants with modulated oligomerization characteristics as compared to wild type. Also provided are fragments of the nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

BREIF DESCRIPTION OF THE FIGURES

FIG. 1 provides the *Heteractic crispa* wild type sequence for the base isoform hcFP640 (hcCP) DNA and the chromoprotein encoded thereby.

FIG. 2 provides the *Heteractic crispa* wild type sequence for the second isoform hcFP640 (hcCP) cDNA and the chromoprotein encoded thereby.

FIG. 3 provides a graph of the absorption spectra for the hcFP640 (hcCP) and C148S mutant proteins.

FIG. 4 provides the nucleic acid sequence for the C148S mutant and the fluorescent protein encoded thereby (C148S according to GFP numbering: C143S according to self-numbering).

Figure 5A:
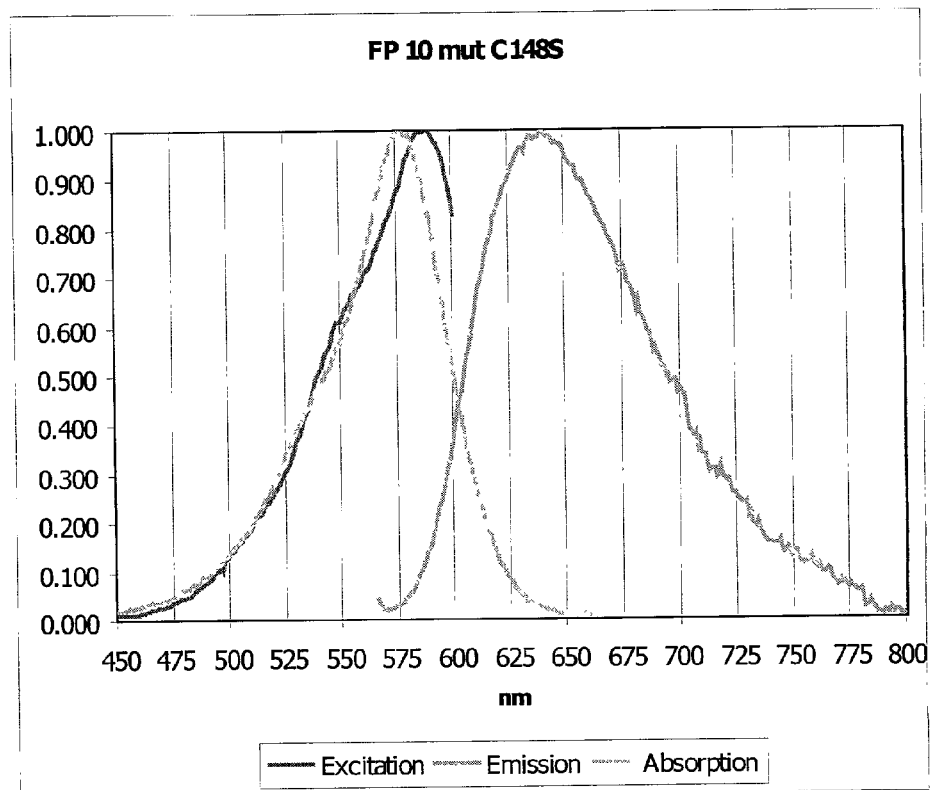
Figure 5B:
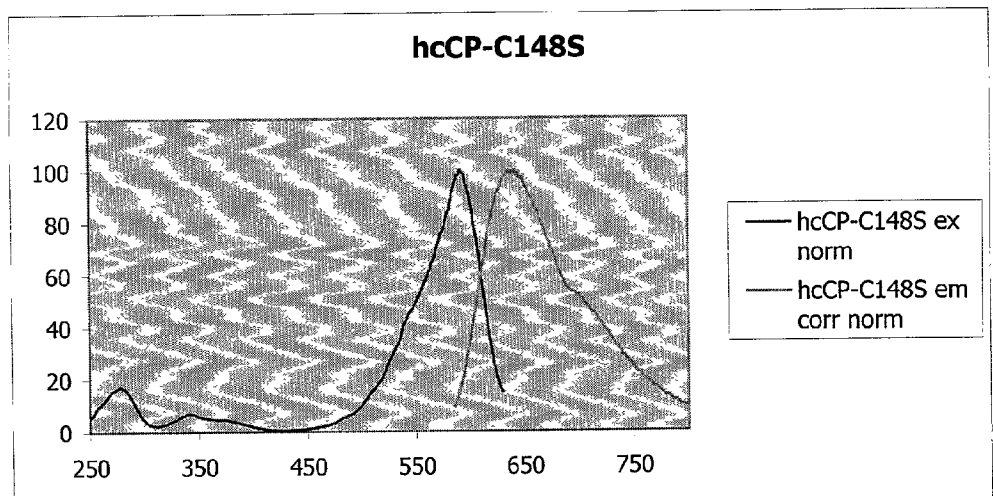

FIGS. 5a and 5b provide graphs of the absorption, excitation and emission spectra for the C148S mutant protein.

FIG. 6 provides the nucleic acid sequence for the 44-9 (hcFRFP) (hcCP) mutant and the fluorescent protein encoded thereby (A5S, T39A, C148S, L181H, P208L, K211E according to GFP numbering; A2S, T36A, C143S, L173H, P201L, K204E according to self-numbering).

Figure 7A:
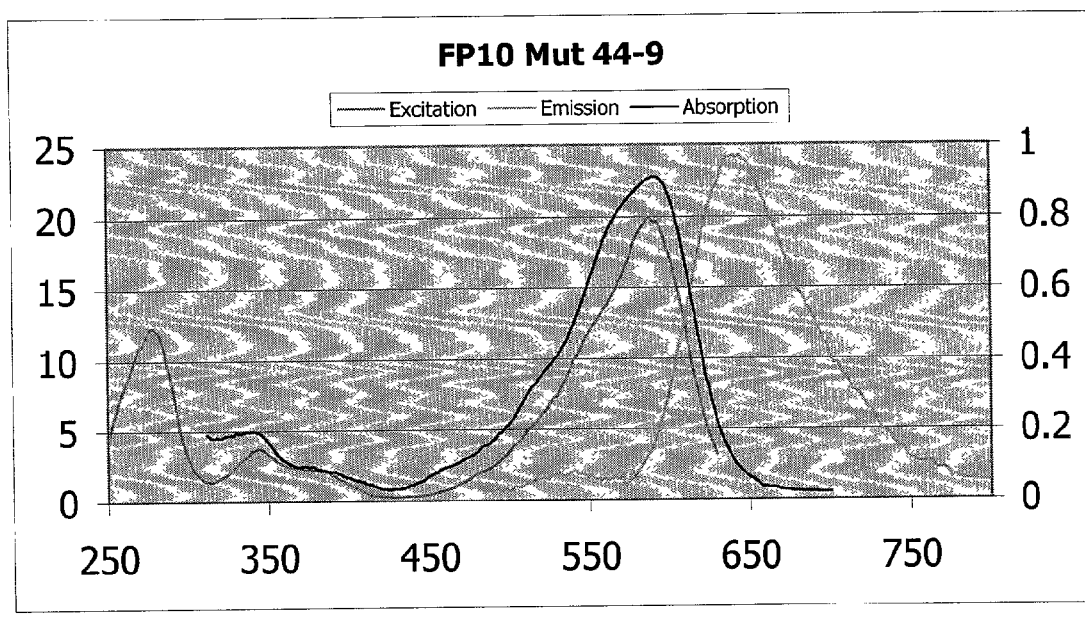
Figure 7B:
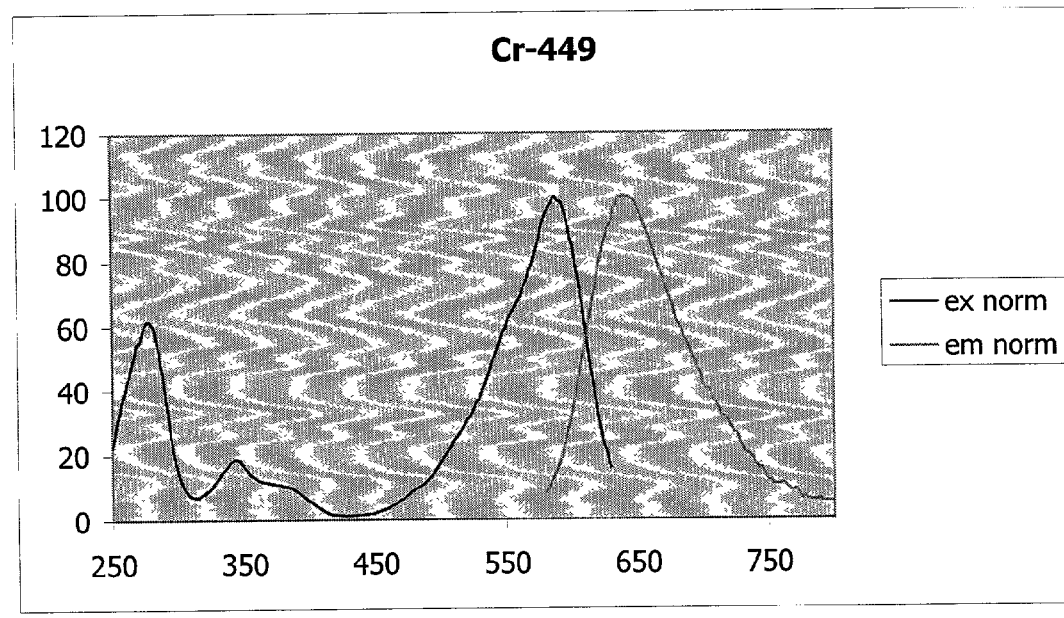

FIGS. 7a and 7b provide graphs of the absorption, excitation and emission spectra for the 44-9 mutant protein.

FIG. 8 provides the amino acid sequence and a nucleotide encoding sequence for the mutant 44-6 described herein. The Crispa 44-6 mutant possesses six amino acid substitutions vs. wild type: A2S, E63A, C143S, L173H, P201L.

Figure 9:
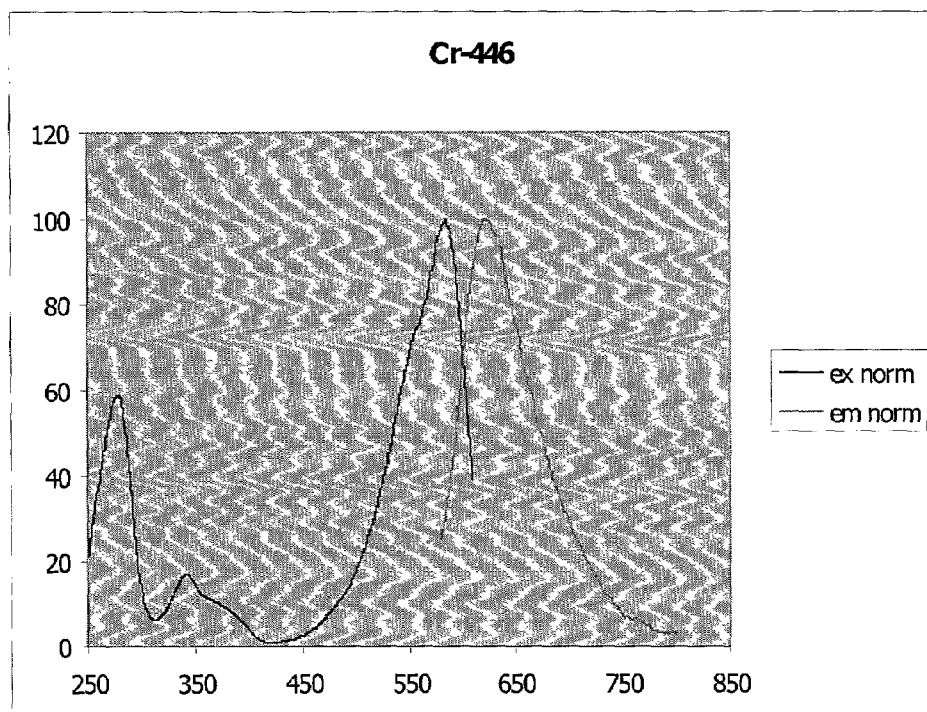

FIG. 9 provides a graph of the excitation and emission spectra for the 44-6 mutant protein.

FIG. 10 provides the amino acid and nucleic acid sequence for the mutant FP10-cr1 (hcFRFP-2) (HcRed-2A). Panel A is the amino acid seguence of FP10cr1. Panel B is a "humanized" nucleotide seguence encoding the FP10cr1mutant of Panel A. Panel C is an alternative cr1 amino acid. Panel D is the amino acid seguence encoding the alternative seguence of Panel C.

Figure 11:
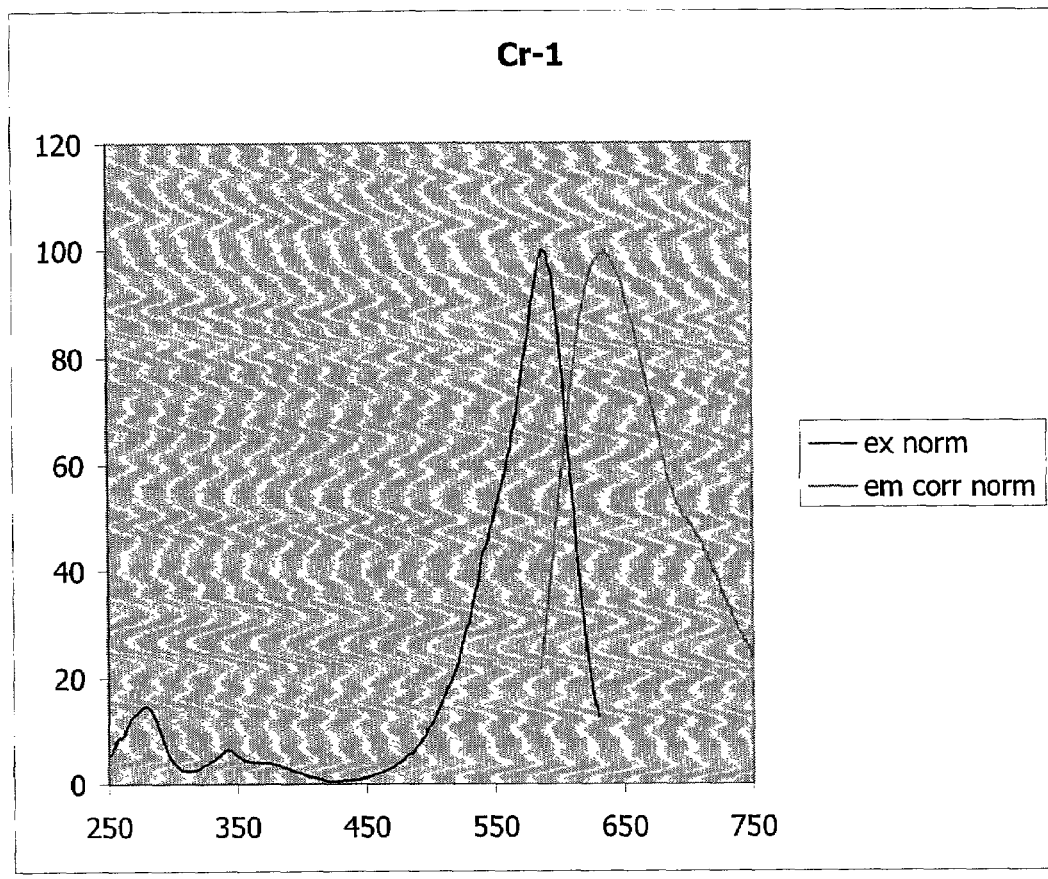

FIG. 11 provides a graph of the excitation and emission spectra for the cr-1 protein.

FIG. 12 provides the amino acid and encoding nucleotide sequence for the Cr-449-tandem fusion protein (the 4-amino acid linker between monomers is in double underline).

FIG. 13 provides the amino acid and encoding nucleotide sequence for the Cr-449-tandem-actin fusion protein according to the subject invention (the 4-amino acid linker between Cr-449 monomers is noted in double underline; the 4-amino acid linker between the second Cr-449 and actin is noted in dashed underline).

Figure 14:
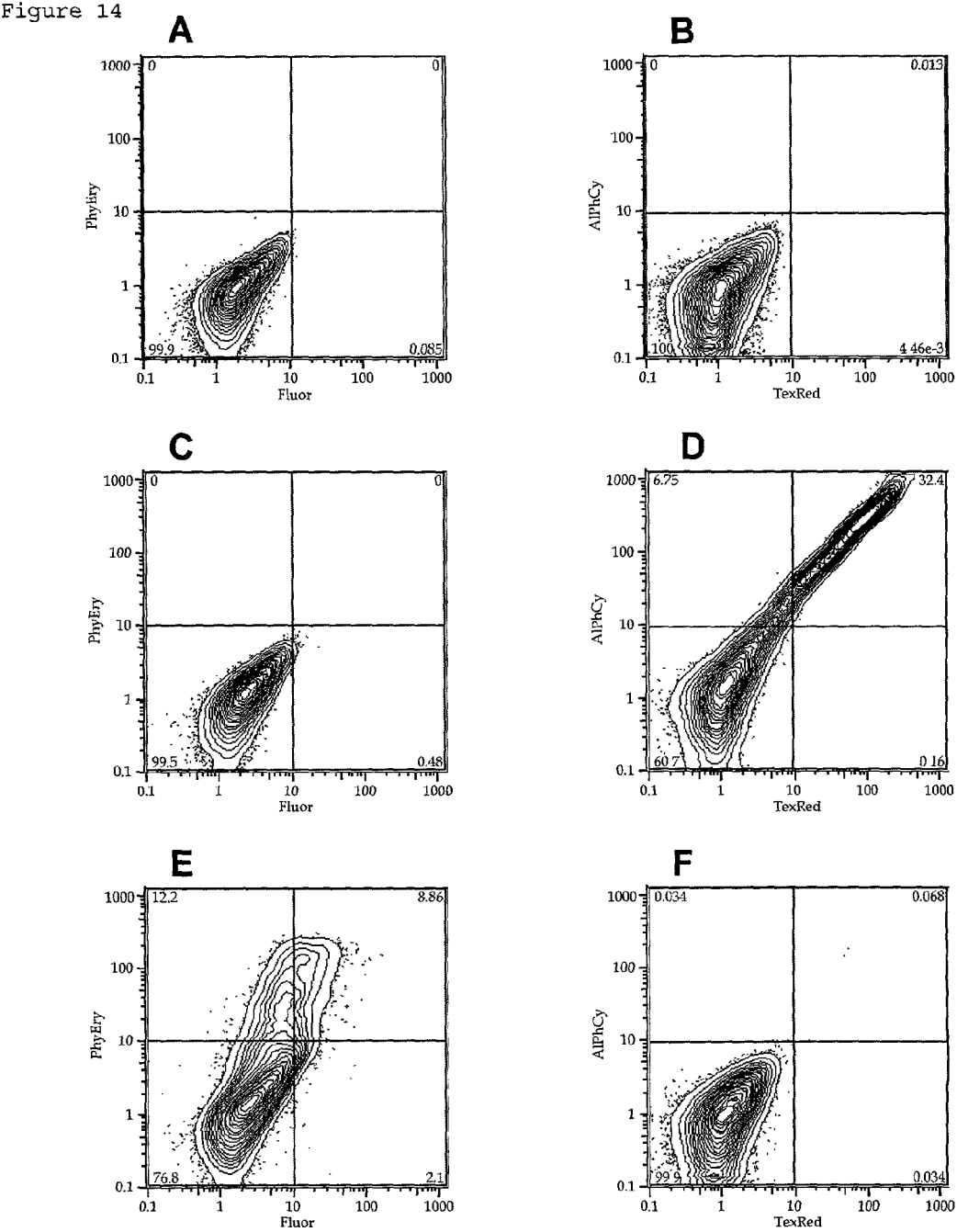

FIG. 14 provides the results of a flow cytometry analysis reported in the experimental section, below.

FIG. 15 provides the amino acid and nucleotide sequence of an alternative embodiment of c1485 (C148S according to GFP numbering; C143S according to self-numbering).

FIG. 16 provides the amino acid and nucleotide sequence of an alternative embodiment of 44-6. The crispa 44-6 mutant possess six amino acid substitutions vs. wild type: A2S, T36A, E63A, C143S, L173H, P201L.

FIG. 17 provides the amino acid and nucleotide sequence of an alternative embodiment of the wild type *Hetaractis crisna* base isoform hcCP.

DEFINITIONS

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

As used herein, the term "hybridization" refers to the process of association of two nucleic acid strands to form an antiparallel duplex stabilized by means of hydrogen bonding between residues of the opposite nucleic acid strands.

The term "oligonucleotide" refers to a short (under 100 bases in length) nucleic acid molecule.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to heterologous promoter or enhancer elements and whose product may be assayed easily and quantifiably when the construct is introduced into tissues or cells.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243 (1969), 3552–59 is used.

The term "immunologically active" defines the capability of the natural, recombinant or synthetic chromo/fluorescent protein, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal. The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a polypeptide, an antibody, or a host cell that is in an environment different from that in which the polynucleotide, the polypeptide, the antibody, or the host cell naturally occurs.

DESCRIPTION OF THE SPECIFIC EMBODIMENTS

Nucleic acid compositions encoding far-red shifted fluorescent proteins, including Stichodactylidaen fluorescent mutants, as well as the polypeptide compositions encoded by the same, are provided. The proteins of interest are proteins that are colored and/or fluorescent, where this feature arises from the interaction of two or more residues of the protein. Also of interest are proteins that are substantially similar to, or mutants of, the above specific proteins, including non-aggregating mutants and mutants with modulated oligomerization characteristics as compared to wild type. Also provided are fragments of the nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described. All publications mentioned herein are incorporated herein by reference for the purpose of describing and disclosing the cell lines, vectors, methodologies and other invention components that are described in the publications which might be used in connection with the presently described invention.

In further describing the subject invention, the subject nucleic acid compositions will be described first, followed by a discussion of the subject protein compositions, antibody compositions and transgenic cells/organisms. Next a review of representative methods in which the subject proteins find use is provided.

Nucleic Acid Compositions

As summarized above, the subject invention provides nucleic acid compositions encoding far red shifted fluorescent proteins, which proteins include fluorescent mutants of Stichodactylidaen chromoproteins, including far red shifted fluorescent mutants thereof, as well as fragments and homologues of these proteins. By chromo and/or fluorescent protein is meant a protein that is colored, i.e., is pigmented, where the protein may or may not be fluorescent, e.g., it may exhibit low, medium or high fluorescence upon irradiation. In any event, the subject proteins of interest are those in which the colored characteristic, i.e., the chromo and/or fluorescent characteristic, is one that arises from the interaction of two or more residues of the protein, and not from a single residue, more specifically a single side chain of a single residue, of the protein. As such, fluorescent proteins of the subject invention do not include proteins that exhibit fluorescence only from residues that act by themselves as intrinsic fluors, i.e., tryptophan, tyrosine and phenylalanine. As such, the fluorescent proteins of the subject invention are fluorescent proteins whose fluorescence arises from some structure in the protein that is other than the above specified single residues, e.g., it arises from an interaction of two or more residues.

By nucleic acid composition is meant a composition comprising a sequence of DNA having an open reading frame that encodes a chromo/fluoro polypeptide of the subject invention, e.g., a Stichodactylidaen chromo/fluoroprotein gene, and is capable, under appropriate conditions, of being expressed as a protein according to the subject invention. Also encompassed in this term are nucleic acids that are homologous, substantially similar or identical to the nucleic acids of the present invention. Thus, the subject invention provides genes and coding sequences thereof encoding the proteins of the subject invention, as well as homologs thereof. The subject nucleic acids are present in other than their natural environment, e.g., they are isolated, present in enriched amounts, etc., from their naturally occurring environment, e.g., the organism from which they are obtained.

In many embodiments, the wild type naturally occurring nucleic acid sequences of the subject invention are from specie members of the family Stichodactylidae, and in certain embodiments from the genus Heteractis. Species of particular interest include *Heteractis magnifica, Heteractis malu, Heteractis crispa, Heteractis aurora,* Heteractis sp. etc., where in many embodiments the wild type nucleic acids are from *Heteractis crispa.*

A specific nucleic acid of interest is one that encodes the wild type chromoprotein of *Heteractis crispa* identified herein as hcFP640 or hcCP (hcCP). Two isoforms of this protein have been identified, i.e., the base isoform and the second isoform. The base isoform has the amino acid sequence shown in FIG. 1 and identified as SEQ ID NO:02. The second isoform has the amino acid sequence shown in FIG. 2 and identified as SEQ ID NO:04. The wild type cDNA coding sequence for the hcFP640 (hcCP) base isoform is provided in SEQ ID NO: 01 and is shown in FIG. 1. The wild type cDNA coding sequence for hcFP640 (hcCP) second isoform is provided in SEQ ID NO: 03 and is shown in FIG. 2.

Nucleic acids encoding specific fluorescent mutant proteins of the above wild type chromoproteins are also provided. Of particular interest are nucleic acids encoding mutant fluorescent proteins identified herein as mutC148S, mut 44-9 (hcFRFP) (HcRed); mut FP10-cr1 (hcFRFP-2) (HcRed-2A), mut hc-44, mut hc-4, mut hc-41 and mut-44-6.

In addition to the above described specific nucleic acid compositions, also of interest are homologues of the above sequences. With respect to homologues of the subject nucleic acids, the source of homologous genes may be any species of plant or animal, or the homologue may be a completely synthetic sequence. In certain embodiments, sequence similarity between homologues is at least about 20%, sometimes at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings, i.e. parameters w=4 and T=17). The sequences provided herein are essential for recognizing related and homologous nucleic acids in database searches. Of particular interest in certain embodiments are nucleic acids of substantially the same length as the specific nucleic acids identified in the enclosed sequence listing and provided in the enclosed figures, where by substantially the same length is meant that any difference in length does not exceed about 20 number %, usually does not exceed about 10 number % and more usually does not exceed about 5 number %; and have sequence identity to any of these sequences of at least about 90%, usually at least about 95% and more usually at least about 99% over the entire length of the nucleic acid. In many embodiments, the nucleic acids have a sequence that is substantially similar (i.e. the same as) or identical to the specific nucleic acid sequences of the figures and sequence listing included herewith as part of this specification. By substantially similar is meant that sequence identity will generally be at least about 60%, usually at least about 75% and often at least about 80, 85, 90, or even 95%.

Also provided are nucleic acids that encode the proteins encoded by the above described nucleic acids, but differ in sequence from the above described nucleic acids due to the degeneracy of the genetic code.

Also provided are nucleic acids that hybridize to the above described nucleic acids under stringent conditions. An example of stringent hybridization conditions is hybridization at 50° C. or higher and 0.1× SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

Nucleic acids encoding mutants of the proteins of the invention are also provided. Mutant nucleic acids can be generated by random mutagenesis or targeted mutagenesis, using well-known techniques that are routine in the art. In some embodiments, chromo- or fluorescent proteins encoded by nucleic acids encoding homologues or mutants have the same fluorescent properties as the wild-type fluorescent protein. In other embodiments, homologue or mutant nucleic acids encode chromo- or fluorescent proteins with altered spectral properties, as described in more detail herein.

One category of mutant that is of particular interest is the non-aggregating mutant. In many embodiments, the non-aggregating mutant differs from the wild type sequence by a mutation in the N-terminus that modulates the charges appearing on side groups of the N-terminus residues, e.g., to reverse or neutralize the charge, in a manner sufficient to produce a non-aggregating mutant of the naturally occurring protein or mutant, where a particular protein is considered to be non-aggregating if it is determined be non-aggregating using the assay reported in U.S. patent application Ser. No. 60/270,983, the disclosure of which is herein incorporated by reference.

Another category of mutant of particular interest is the modulated oligomerization mutant. A mutant is considered to be a modulated oligomerization mutant if its oligomerization properties are different as compared to the wild type protein. For example, if a particular mutant oligomerizes to a greater or lesser extent than the wild type, it is considered to be an oligomerization mutant. Of particular interest are oligomerization mutants that do not oligomerize, i.e., are monomers under physiological (e.g., intracellular) conditions, or oligomerize to a lesser extent that the wild type, e.g., are dimers or trimers under intracellular conditions.

Nucleic acids of the subject invention may be cDNA or genomic DNA or a fragment thereof. In certain embodiments, the nucleic acids of the subject invention include one or more of the open reading frames encoding specific fluorescent proteins and polypeptides, and introns, as well as adjacent 5' and 3' non-coding nucleotide sequences involved in the regulation of expression, up to about 20 kb beyond the coding region, but possibly further in either direction. The subject nucleic acids may be introduced into an appropriate vector for extrachromosomal maintenance or for integration into a host genome, as described in greater detail below.

The term "cDNA" as used herein is intended to include all nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest comprises the nucleic acid present between the initiation codon and the stop codon, as defined in the listed sequences, including all of the introns that are normally present in a native chromosome. It may further include 5' and 3' un-translated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject proteins. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least about 15 nt, usually at least about 18 nt or about 25 nt, and may be at least about 50 nt. In some embodiments, the subject nucleic acid molecules may be about 100 nt, about 200 nt, about 300 nt, about 400 nt, about 500 nt, about 600 nt, about 700 nt, or about 720 nt in length. The subject nucleic acids may encode fragments of the subject proteins or the full-length proteins, e.g., the subject nucleic acids may encode polypeptides of about 25 aa, about 50 aa, about 75 aa, about 100 aa, about 125 aa, about 150 aa, about 200 aa, about 210 aa, about 220 aa, about 230 aa, or about 240 aa, up to the entire protein.

The subject nucleic acids are isolated and obtained in substantial purity, generally as other than an intact chromosome. Usually, the DNA will be obtained substantially free of other nucleic acid sequences that do not include a nucleic acid of the subject invention or fragment thereof, generally being at least about 50%, usually at least about 90% pure and are typically "recombinant", i.e. flanked by one or more nucleotides with which it is not normally associated on a naturally occurring chromosome.

The subject polynucleotides, the corresponding cDNA, the full-length gene and constructs of the subject polynucleotides are provided. These molecules can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual, 2nd Ed.*, (1989) Cold Spring Harbor Press, Cold Spring Harbor, N.Y., and under current regulations described in United States Dept. of HHS, National Institute of Health (NIH) Guidelines for Recombinant DNA Research.

Also provided are nucleic acids that encode fusion proteins of the subject proteins, or fragments thereof, which are fused to a second protein, e.g., a degradation sequence, a signal peptide, etc. Fusion proteins may comprise a subject polypeptide, or fragment thereof, and a non-Stichodactylidaen polypeptide ("the fusion partner") fused in-frame at the N-terminus and/or C-terminus of the subject polypeptide. Fusion partners include, but are not limited to, polypeptides that can bind antibody specific to the fusion partner (e.g., epitope tags); antibodies or binding fragments thereof; polypeptides that provide a catalytic function or induce a cellular response; ligands or receptors or mimetics thereof; and the like. In such fusion proteins, the fusion partner is generally not naturally associated with the subject Anthozoan portion of the fusion protein, and is typically not an Anthozoan protein or derivative/fragment thereof, i.e., it is not found in Anthozoan species.

Also provided are constructs comprising the subject nucleic acids inserted into a vector, where such constructs may be used for a number of different applications, including propagation, protein production, etc. Viral and non-viral vectors may be prepared and used, including plasmids. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the subject proteins. For expression, the gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, a subject polynucleotide, is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described above.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, Xenopus Oocytes, etc., may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci. (USA)* (1983) 80:21–25; and Siebenlist et al., *Cell* (1980) 20:269.

Yeast. Expression systems in yeast include those described in Hinnen et al., *Proc. Natl. Acad. Sci. (USA)* (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154: 737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., Curr. Genet. (1985) 10:49; Ballance et al., *Biochem. Biophys. Res. Commun.* (1983) 112:284–289; Tilburn et al., *Gene* (1983) 26:205–221; Yelton et al., *Proc. Natl. Acad. Sci. (USA)* (1984) 81:1470–1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Viak et al., *J. Gen. Virol.* (1988) 69:765–776; Miller et al., *Ann. Rev. Microbiol.* (1988) 42:177; Carbonell et al., *Gene* (1988) 73:409; Maeda et al., *Nature* (1985) 315:592–594; Lebacq-Verheyden et al., *Mol. Cell. Biol.* (1988) 8:3129; Smith et al., *Proc. Natl. Acad. Sci. (USA)* (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594.

Mammalian Cells. Mammalian expression is accomplished as described in Dijkema et al., *EMBO J.* (1985) 4:761, Gorman et al., *Proc. Natl. Acad. Sci. (USA)* (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE. Pat No. No. 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of the subject proteins without manipulation of the encoding nucleic acid itself, but instead through integration of a regulatory sequence into the genome of cell that already includes a gene encoding the desired protein, as described in the above incorporated patent documents.

Also provided are homologs of the subject nucleic acids. Homologs are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/1.5 mM sodium citrate). Nucleic acids having a region of substantial identity to the provided sequences, e.g. allelic variants, genetically altered versions of the gene, etc., bind to the provided sequences under stringent hybridization conditions. By using probes, particularly labeled probes of DNA sequences, one can isolate homologous or related genes.

Also of interest are promoter elements of the subject genomic sequences, where the sequence of the 5' flanking region may be utilized for promoter elements, including enhancer binding sites, e.g., that provide for regulation of expression in cells/tissues where the subject proteins gene are expressed.

Also provided are small DNA fragments of the subject nucleic acids, which fragments are useful as primers for PCR, hybridization screening probes, etc. Larger DNA fragments, i.e., greater than 100 nt are useful for production of the encoded polypeptide, as described in the previous section. For use in geometric amplification reactions, such as geometric PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of Anthozoan protein gene expression in the sample.

The subject nucleic acids, including flanking promoter regions and coding regions, may be mutated in various ways known in the art to generate targeted changes in promoter strength, sequence of the encoded protein, properties of the encoded protein, including fluorescent properties of the encoded protein, etc. The DNA sequence or protein product of such a mutation will usually be substantially similar to the sequences provided herein, e.g. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon, e.g. of stretches of 10, 20, 50, 75, 100, 150 or more aa residues. Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Such mutated nucleic acid derivatives may be used to study structure-function relationships of a particular chromo/fluorescent protein, or to alter properties of the protein that affect its function or regulation.

Of particular interest in many embodiments is the following specific mutation protocol, which protocol finds use in mutating chromoproteins (e.g., colored proteins that have little if any fluorescence) into fluorescent mutants. In this protocol., the sequence of the candidate protein is aligned with the amino acid sequence of *Aequorea victoria* wild type GFP, according to the protocol reported in Matz et al., "Fluorescent proteins from non-bioluminescent Anthozoa species," Nature Biotechnology (October 1999) 17: 969–973. Residue 148 of the aligned chromoprotein is identified and then changed to Ser, e.g., by site directed mutagenesis, which results in the production of a fluorescent mutant of the wild type chromoprotein. See e.g., mut C148S described below.

Also of interest are humanized versions of the subject nucleic acids. As used herein, the term "humanized" refers to changes made to a nucleic acid sequence to optimize the codons for expression of the protein in human cells (Yang et al., *Nucleic Acids Research* 24 (1996), 4592–4593). See also U.S. Pat. No. 5,795,737 which describes humanization of proteins, the disclosure of which is herein incorporated by reference.

Protein/Polypeptide Compositions

Also provided by the subject invention are far red shifted fluorescent proteins, including Stichodactylidaen fluorescent proteins (as well as wild type non-fluorescent chromoprotein precursors thereof) and mutants thereof, as well as polypeptide compositions related thereto. As the subject proteins are chromoproteins, they are colored proteins, which may be fluorescent, low or non-fluorescent. As used herein, the terms chromoprotein and fluorescent protein do not include luciferases, such as Renilla luciferase, and refer to any protein that is pigmented or colored and/or fluoresces when irradiated with light, e.g., white light or light of a specific wavelength (or narrow band of wavelengths). The term polypeptide composition as used herein refers to both the full-length protein, as well as portions or fragments thereof. Also included in this term are variations of the naturally occurring protein, where such variations are homologous or substantially similar to the naturally occurring protein, and mutants of the naturally occurring proteins, as described in greater detail below. The subject polypeptides are present in other than their natural environment.

With respect to the subject proteins that exhibit fluorescence, by which is meant that they can be excited at one wavelength of light following which they will emit light at another wavelength, the excitation spectrum of the subject proteins typically ranges from about 450 to 650, usually from about 550 to 600 and more usually from about 570 to 600 nm while the emission spectrum of the subject proteins typically ranges from about 480 to 680, usually from about 580 to 660 and more usually from about 590 to 650 nm, and in certain of these embodiments ranges from about 620 to 680, usually from about 630 to 670 and more usually from about 635 to 665 nm.

Also provided are Stichodactylidaen chromoproteins that are wild type precursors of certain of the far red shifted fluorescent mutants of the present invention, where these chromoproteins have an absorbance maximum ranging from about 450 to 650, usually from about 550 to 600 and more usually from about 565 to 585 nm.

The subject proteins typically range in length from about 200 to 300, usually from about 220 to 250 amino acid residues, and generally have a molecular weight ranging from about 20 to 35, usually from about 25 to 30 kDa.

In certain embodiments, the subject proteins are bright, where by bright is meant that: the chromoproteins and their fluorescent mutants can be detected by common methods (e.g., visual screening, spectrophotometry, spectrofluorometry, fluorescent microscopy, by FACS machines, etc.) Fluorescence brightness of particular fluorescent proteins is determined by its quantum yield multiplied by maximal extinction coefficient. Brightness a chromoproteins may be expressed by its maximal extinction coefficient.

In certain embodiments, the subject proteins fold rapidly following expression in the host cell. By rapidly folding is meant that the proteins achieve their tertiary structure that gives rise to their chromo- or fluorescent quality in a short period of time. In these embodiments, the proteins fold in a period of time that generally does not exceed about 3 days, usually does not exceed about 2 days and more usually does not exceed about 1 day. In certain embodiments the proteins mature in under physiological temperature conditions, e.g., at temperatures ranging from 30 to 40° C., e.g., 37° C.

A specific and representative wild type Stichodactylidaen chromoprotein according to the subject invention is the wild type *Heteractis crispa* chromoprotein. The base isoform of this protein has an amino acid sequence as shown in FIG. 1 and identified as SEQ ID NO:02. The second isoform of this wild type protein has an amino acid sequence as shown in FIG. 2 and identified as SEQ ID NO:04. Representative specific fluorescent mutants thereof are mutC148S, mut 44-9 (hcFRFP) (HcRed); mut FP10-cr1 (hcFRFP-2) (HcRed-2A), mut hc-44, mut hc-4, mut hc-41 and mut-44-6.

Homologs or proteins (or fragments thereof that vary in sequence from the specific amino acid sequences of the subject invention provided herein are also provided. By homolog is meant a protein having at least about 10%, usually at least about 20% and more usually at least about 30%, and in many embodiments at least about 35%, usually at least about 40% and more usually at least about 60% amino acid sequence identity to the protein of the subject invention, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151–153. (Parameters used are ktuple 1, gap penalty 3, window, 5 and diagonals saved 5). In many embodiments, homologues of interest have much higher sequence identify, e.g., 65%, 70%, 75%, 80%, 85%, 90% or higher.

Also provided are proteins that are substantially identical to the wild type protein, where by substantially identical is meant that the protein has an amino acid sequence identity to the sequence of wild type protein of at least about 60%, usually at least about 65% and more usually at least about 70%, where in some instances the identity may be much higher, e.g., 75%, 80%, 85%, 90%, 95% or higher.

In many embodiments, the subject homologues have structural features found in the above provided specific sequences, where such structural features include the β-can fold.

Proteins which are mutants of the above-described naturally occurring proteins are also provided. Mutants may retain biological properties of the wild-type (e.g., naturally occurring) proteins, or may have biological properties which differ from the wild-type proteins. The term "biological property" of the subject proteins includes, but is not limited to, spectral properties, such as absorbance maximum, emission maximum, maximum extinction coefficient, brightness (e.g., as compared to the wild-type protein or another reference protein such as green fluorescent protein from *A. victoria*), and the like; in vivo and/or in vitro stability (e.g., half-life); etc. Mutants include single amino acid changes, deletions of one or more amino acids, N-terminal truncations, C-terminal truncations, insertions, etc.

Mutants can be generated using standard techniques of molecular biology, e.g., random mutagenesis, and targeted mutagenesis. Several mutants are described herein. Given the guidance provided in the Examples, and using standard techniques, those skilled in the art can readily generate a wide variety of additional mutants and test whether a biological property has been altered. For example, fluorescence intensity can be measured using a spectrophotometer at various excitation wavelengths.

Those proteins of the subject invention that are naturally occurring proteins are present in a non-naturally occurring environment, e.g., are separated from their naturally occurring environment. In certain embodiments, the subject proteins are present in a composition that is enriched for the subject protein as compared to its naturally occurring environment. For example, purified protein is provided, where by purified is meant that the protein is present in a composition that is substantially free of non-Stichodactylidaen chromo/fluoroprotein derived proteins, where by substantially free is meant that less than 90%, usually less than 60% and more usually less than 50% of the composition is made up of non-Anthozoan derived chromoproteins or mutants thereof. The proteins of the subject invention may also be present as an isolate, by which is meant that the protein is substantially free of other proteins and other naturally occurring biologic molecules, such as oligosaccharides, polynucleotides and fragments thereof, and the like, where the term "substantially free" in this instance means that less than 70%, usually less than 60% and more usually less than 50% of the composition containing the isolated protein is some other naturally occurring biological molecule. In certain embodiments, the proteins are present in substantially pure form, where by "substantially pure form" is meant at least 95%, usually at least 97% and more usually at least 99% pure.

In addition to the naturally occurring proteins, polypeptides that vary from the naturally occurring proteins, e.g., the mutant proteins described above, are also provided. Generally such polypeptides include an amino acid sequence encoded by an open reading frame (ORF) of the gene encoding an Anthozoan protein, including the full length protein and fragments thereof, particularly biologically active fragments and/or fragments corresponding to functional domains, and the like; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to the subject protein of at least about 10 aa, and usually at least about 15 aa, and in many embodiments at least about 50 aa in length. In some embodiments, the subject polypeptides are about 25 aa, about 50 aa, about 75 aa, about 100 aa, about 125 aa, about 150 aa, about 200 aa, about 210 aa, about 220 aa, about 230 aa, or about 240 aa in length, up to the entire protein. In some embodiments, a protein fragment retains all or substantially all of a biological property of the wild-type protein.

The subject proteins and polypeptides may be obtained from naturally occurring sources or synthetically produced. For example, wild type proteins may be derived from biological sources that express the proteins, e.g., Anthozoan species, such as the specific ones listed above. The subject proteins may also be produced using synthetic means, e.g. by expressing a recombinant gene or nucleic acid coding sequence encoding the protein of interest in a suitable host, as described above. Any convenient protein purification procedures may be employed, where suitable protein purification methodologies are described in Guide to Protein Purification, (Deuthser ed.) (Academic Press, 1990). For example, a lysate may prepared from the original source and purified using HPLC, exclusion chromatography, gel electrophoresis, affinity chromatography, and the like.

Antibody Compositions

Also provided are antibodies that specifically bind to the subject fluorescent proteins. Suitable antibodies are obtained by immunizing a host animal with peptides comprising all or a portion of the subject protein. Suitable host animals include mouse, rat sheep, goat, hamster, rabbit, etc. The origin of the protein immunogen will generally be an Anthozoan species. The host animal will generally be a different species than the immunogen, e.g., mice, etc.

The immunogen may comprise the complete protein, or fragments and derivatives thereof. Preferred immunogens comprise all or a part of the protein, where these residues contain the post-translation modifications found on the native target protein. Immunogens are produced in a variety of ways known in the art, e.g., expression of cloned genes using conventional recombinant methods, isolation from Anthozoan species, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also of interest in certain embodiments are humanized antibodies. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Transgenics

The subject nucleic acids can be used to generate transgenic, non-human plants or animals or site specific gene modifications in cell lines. Transgenic cells of the subject invention include on or more nucleic acids according to the subject invention present as a transgene, where included within this definition are the parent cells transformed to include the transgene and the progeny thereof. In many embodiments, the transgenic cells are cells that do not normally harbor or contain a nucleic acid according to the subject invention. In those embodiments where the transgenic cells do naturally contain the subject nucleic acids, the nucleic acid will be present in the cell in a position other than its natural location, i.e. integrated into the genomic material of the cell at a non-natural location. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

Transgenic organisms of the subject invention include cells and multicellular organisms, e.g., plants and animals, that are endogenous knockouts in which expression of the endogenous gene is at least reduced if not eliminated. Transgenic organisms of interest also include cells and multicellular organisms, e.g., plants and animals, in which the protein or variants thereof is expressed in cells or tissues where it is not normally expressed and/or at levels not normally present in such cells or tissues.

DNA constructs for homologous recombination will comprise at least a portion of the gene of the subject invention, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc. Representative examples of the use of transgenic animals include those described infra.

Transgenic plants may be produced in a similar manner. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants are also reviewed in Plant Biochemistry and Molecular Biology (eds Lea & Leegood, John Wiley & Sons)(1993) pp 275–295. In brief, a suitable plant cell or tissue is harvested, depending on the nature of the plant species. As such, in certain instances, protoplasts will be isolated, where such protoplasts may be isolated from a variety of different plant tissues, e.g. leaf, hypoctyl, root, etc. For protoplast isolation, the harvested cells are incubated in the presence of cellulases in order to remove the cell wall, where the exact incubation conditions vary depending on the type of plant and/or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells, where a variety of different techniques are available for such introduction. With isolated protoplasts, the opportunity arise for introduction via DNA-mediated gene transfer protocols, including: incubation of the protoplasts with naked DNA, e.g. plasmids, comprising the exogenous coding sequence of interest in the presence of polyvalent cations, e.g. PEG or PLO; and electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, e.g. auxins and cytokinins. With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained. Instead of the naked DNA approaches described above, another convenient method of producing transgenic plants is Agrobacterium mediated transformation. With Agrobacterium mediated transformation, co-integrative or binary vectors comprising the exogenous DNA are prepared and then introduced into an appropriate Agrobacterium strain, e.g. A. tumefaciens. The resultant bacteria are then incubated with prepared protoplasts or tissue explants, e.g. leaf disks, and a callus is produced. The callus is then grown under selective conditions, selected and subjected to growth media to induce root and shoot growth to ultimately produce a transgenic plant.

Utility

The subject chromoproteins and fluorescent mutants thereof find use in a variety of different applications, where the applications necessarily differ depending on whether the protein is a chromoprotein or a fluorescent protein. Representative uses for each of these types of proteins will be described below, where the follow described uses are merely representative and are in no way meant to limit the use of the subject proteins to those described below.

Chromoproteins

The subject chromoproteins of the present invention find use in a variety of different applications. One application of interest is the use of the subject proteins as coloring agents which are capable of imparting color or pigment to a particular composition of matter. Of particular interest in certain embodiments are non-toxic chromoproteins. The subject chromoproteins may be incorporated into a variety of different compositions of matter, where representative compositions of matter include: food compositions, pharmaceuticals, cosmetics, living organisms, e.g., animals and plants, and the like. Where used as a coloring agent or pigment, a sufficient amount of the chromoprotein is incorporated into the composition of matter to impart the desired color or pigment thereto. The chromoprotein may be incorporated into the composition of matter using any convenient protocol, where the particular protocol employed will necessarily depend, at least in part, on the nature of the composition of matter to be colored. Protocols that may be employed include, but are not limited to: blending, diffusion, friction, spraying, injection, tattooing, and the like.

The chromoproteins may also find use as labels in analyte detection assays, e.g., assays for biological analytes of interest. For example, the chromoproteins may be incorporated into adducts with analyte specific antibodies or binding fragments thereof and subsequently employed in immunoassays for analytes of interest in a complex sample, as described in U.S. Pat. No. 4,302,536; the disclosure of which is herein incorporated by reference. Instead of antibodies or binding fragments thereof, the subject chromoproteins or chromogenic fragments thereof may be conjugated to ligands that specifically bind to an analyte of interest, or other moieties, growth factors, hormones, and the like; as is readily apparent to those of skill in the art.

In yet other embodiments, the subject chromoproteins may be used as selectable markers in recombinant DNA applications, e.g., the production of transgenic cells and organisms, as described above. As such, one can engineer a particular transgenic production protocol to employ expression of the subject chromoproteins as a selectable marker, either for a successful or unsuccessful protocol. Thus, appearance of the color of the subject chromoprotein in the phenotype of the transgenic organism produced by a particular process can be used to indicate that the particular organism successfully harbors the transgene of interest, often integrated in a manner that provides for expression of the transgene in the organism. When used a selectable marker, a nucleic acid encoding for the subject chromoprotein can be employed in the transgenic generation process, where this process is described in greater detail supra. Particular transgenic organisms of interest where the subject proteins may be employed as selectable markers include transgenic plants, animals, bacteria, fungi, and the like.

In yet other embodiments, the chromoproteins (and fluorescent proteins) of the subject invention find use in sunscreens, as selective filters, etc., in a manner similar to the uses of the proteins described in WO 00/46233.

Fluorescent Proteins

The subject fluorescent proteins of the present invention (as well as other components of the subject invention described above) find use in a variety of different applications, where such applications include, but are not limited to, the following. The first application of interest is the use of the subject proteins in fluorescence resonance energy transfer (FRET) applications. In these applications, the subject proteins serve as donor and/or acceptors in combination with a second fluorescent protein or dye, e.g., a fluorescent protein as described in Matz et al., Nature Biotechnology (October 1999) 17:969–973, a green fluorescent protein from *Aequoria victoria* or fluorescent mutant thereof, e.g., as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference, other fluorescent dyes, e.g., coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemilumescent dyes, e.g., luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference. Specific examples of where FRET assays employing the subject fluorescent proteins may be used include, but are not limited to: the detection of protein-protein interactions, e.g., mammalian two-hybrid system, transcription factor dimerization, membrane protein multimerization, multiprotein complex formation, etc., as a biosensor for a number of different events, where a peptide or protein covalently links a FRET fluorescent combination including the subject fluorescent proteins and the linking peptide or protein is, e.g., a protease specific substrate, e.g., for caspase mediated cleavage, a linker that undergoes conformational change upon receiving a signal which increases or decreases FRET, e.g., PKA regulatory domain (cAMP-sensor), phosphorylation, e.g., where there is a phosphorylation site in the linker or the linker has binding specificity to phosphorylated/dephosphorylated domain of another protein, or the linker has $Ca^{2+}$ binding domain. Representative fluorescence resonance energy transfer or FRET applications in which the subject proteins find use include, but are not limited to, those described in: U.S. Pat. Nos. 6,008,373; 5,998,146; 5,981,200; 5,945,526; 5,945,283; 5,911,952; 5,869,255; 5,866, 336; 5,863,727; 5,728,528; 5,707,804; 5,688,648; 5,439,797; the disclosures of which are herein incorporated by reference.

The subject fluorescent proteins also find use as biosensors in prokaryotic and eukaryotic cells, e.g. as $Ca^{2+}$ ion indicator; as pH indicator, as phorphorylation indicator, as an indicator of other ions, e.g., magnesium, sodium, potassium, chloride and halides. For example, for detection of Ca ion, proteins containing an EF-hand motif are known to translocate from the cytosol to membranes upon $Ca^{2+}$ binding. These proteins contain a myristoyl group that is buried within the molecule by hydrophobic interactions with other regions of the protein. Binding of $Ca^{2+}$ induces a conformational change exposing the myristoyl group which then is available for the insertion into the lipid bilayer (called a "$Ca^{2+}$-myristoyl switch"). Fusion of such a EF-hand containing protein to Fluorescent Proteins (FP) could make it an indicator of intracellular $Ca^{2+}$ by monitoring the translocation from the cytosol to the plasma membrane by confocal microscopy. EF-hand proteins suitable for use in this system include, but are not limited to: recoverin (1–3), calcineurin B, troponin C, visinin, neurocalcin, calmodulin, parvalbumin, and the like. For pH, a system based on hisactophilins may be employed. Hisactophilins are myristoylated histidine-rich proteins known to exist in *Dictyostelium*. Their binding to actin and acidic lipids is sharply pH-dependent within the range of cytoplasmic pH variations. In living cells membrane binding seems to override the interaction of hisactophilins with actin filaments. At pH 6.5 they locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By fusing FPs (Fluoresent Proteins) to hisactophilin the intracellular distribution of the fusion protein can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells. Substantial pH-dependent redistribution of hisactophilin-FP from the cytosol to the plasma membrane occurs within 1–2 min and reaches a steady state level after 5–10 min. The reverse reaction takes place on a similar time scale. As such, hisactophilin-fluorescent protein fusion protein that acts in an analogous fashion can be used to monitor cytosolic pH changes in real time in live mammalian cells. Such methods have use in high throuhgput applications, e.g., in the measurement of pH changes as consequence of growth factor receptor activation (e.g. epithelial or platelet-derived growth factor) chemotactic stimulation/cell locomotion, in the detection of intracellular pH changes as second messenger, in the monitoring of intracellular pH in pH manipulating experiments, and the like. For detection of PKC activity, the reporter system exploits the fact that a molecule called MARCKS (myristoylated alanine-rich C kinase substrate) is a PKC substrate. It is anchored to the plasma membrane via myristoylation and a stretch of positively charged amino acids (ED-domain) that bind to the negatively charged plasma membrane via electrostatic interactions. Upon PKC activation the ED-domain becomes phosphorylated by PKC, thereby becoming negatively charged, and as a consequence of electrostatic repulsion MARCKS translocates from the plasma membrane to the cytoplasm (called the "myristoyl-electrostatic switch"). Fusion of the N-terminus of MARCKS ranging from the myristoylation motif to the ED-domain of MARCKS to fluorescent proteins of the present invention makes the above a detector system for PKC activity. When phosphorylated by PKC, the fusion protein translocates from the plasma membrane to the cytosol. This translocation is followed by standard fluorescence microscopy or confocal microscopy e.g. using the Cellomics technology or other High Content Screening systems (e.g. Universal Imaging Corp./Becton Dickinson). The above reporter system has application in High Content Screening, e.g., screening for PKC inhibitors, and as an indicator for PKC activity in many screening scenarios for potential reagents interfering with this signal transduction pathway. Methods of using fluorescent proteins as biosensors also include those described in U.S. Pat. Nos. 972,638; 5,824,485 and 5,650,135 (as well as the references cited therein) the disclosures of which are herein incorporated by reference.

The subject fluorescent proteins also find use in applications involving the automated screening of arrays of cells expressing fluorescent reporting groups by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth, etc.; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B1 and cyclinE; protease cleavage with subsequent movement of cleaved substrate, phospholipids, with markers for intracellular structures such as endoplasmic reticulum, Golgi apparatus, mitochondria, peroxisomes, nucleus, nucleoli, plasma membrane, histones, endosomes, lysosomes, microtubules, actin) as tools for High Content Screening: co-localization of other fluorescent fusion proteins with these localization markers as indicators of movements of intracellular fluorescent fusion proteins/peptides or as marker alone; and the like. Examples of applications involving the automated screening of arrays of cells in which the subject fluorescent proteins find use include: U.S. Pat. No. 5,989,835; as well as WO/0017624; WO 00/26408; WO 00/17643; and WO 00/03246; the disclosures of which are herein incorporated by reference.

The subject fluorescent proteins also find use in high through-put screening assays. The subject fluorescent proteins are stable proteins with half-lives of more than 24 h. Also provided are destabilized versions of the subject fluorescent proteins with shorter half-lives that can be used as transcription reporters for drug discovery. For example, a protein according to the subject invention can be fused with a putative proteolytic signal sequence derived from a protein with shorter half-life, e.g., PEST sequence from the mouse ornithine decarboxylase gene, mouse cyclin B1 destruction box and ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject fluorescent proteins for drug screening, e.g., AP1, NFAT, NFkB, Smad, STAT, p53, E2F, Rb, myc, CRE, ER, GR and TRE, and the like.

The subject proteins can be used as second messenger detectors, e.g., by fusing the subject proteins to specific domains: e.g., PKCgamma Ca binding domain, PKCgamma DAG binding domain, SH2 domain and SH3 domain, etc.

Secreted forms of the subject proteins can be prepared, e.g. by fusing secreted leading sequences to the subject proteins to construct secreted forms of the subject proteins, which in turn can be used in a variety of different applications.

The subject proteins also find use in fluorescence activated cell sorting applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo marker in animals (e.g., transgenic animals). For example, expression of the subject protein can be driven by tissue specific promoters, where such methods find use in research for gene therapy, e.g., testing efficiency of transgenic expression, among other applications. A representative application of fluorescent proteins in transgenic animals that illustrates this class of applications of the subject proteins is found in WO 00/02997, the disclosure of which is herein incorporated by reference.

Additional applications of the subject proteins include: as markers following injection into cells or animals and in calibration for quantitative measurements (fluorescence and protein); as markers or reporters in oxygen biosensor devices for monitoring cell viability; as markers or labels for animals, pets, toys, food, etc.; and the like.

The subject fluorescent proteins also find use in protease cleavage assays. For example, cleavage inactivated fluorescence assays can be developed using the subject proteins, where the subject proteins are engineered to include a protease specific cleavage sequence without destroying the fluorescent character of the protein. Upon cleavage of the fluorescent protein by an activated protease fluorescence would sharply decrease due to the destruction of a functional chromophor. Alternatively, cleavage activated fluorescence can be developed using the subject proteins, where the subject proteins are engineered to contain an additional spacer sequence in close proximity/or inside the chromophor. This variant would be significantly decreased in its fluorescent activity, because parts of the functional chromophor would be divided by the spacer. The spacer would be framed by two identical protease specific cleavage sites. Upon cleavage via the activated protease the spacer would be cut out and the two residual "subunits" of the fluorescent protein would be able to reassemble to generate a functional fluorescent protein. Both of the above types of application could be developed in assays for a variety of different types of proteases, e.g., caspases, etc.

The subject proteins can also be used is assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes also allowing colocalization of membrane proteins in specific phospholipid rafts can be accomplished with the subject proteins. For example, the PH domain of GRP1 has a high affinity to phosphatidylinositol tri-phosphate (PIP3) but not to PIP2. As such, a fusion protein between the PH domain of GRP1 and the subject proteins can be constructed to specifically label PIP3 rich areas in biological membranes.

Yet another application of the subject proteins is as a fluorescent timer, in which the switch of one fluorescent color to another (e.g. green to red) concomitant with the ageing of the fluorescent protein is used to determine the activation/deactivation of gene expression, e.g., developmental gene expression, cell cycle dependent gene expression, circadian rhythm specific gene expression, and the like.

The antibodies of the subject invention, described above, also find use in a number of applications, including the differentiation of the subject proteins from other fluorescent proteins.

Kits

Also provided by the subject invention are kits for use in practicing one or more of the above described applications, where the subject kits typically include elements for making the subject proteins, e.g., a construct comprising a vector that includes a coding region for the subject protein. The subject kit components are typically present in a suitable storage medium, e.g., buffered solution, typically in a suitable container. Also present in the subject kits may be antibodies to the provided protein. In certain embodiments, the kit comprises a plurality of different vectors each encoding the subject protein, where the vectors are designed for expression in different environments and/or under different conditions, e.g., constitutive expression where the vector includes a strong promoter for expression in mammalian cells, a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

Experimental

I. Characterization of hcFP640 (hcCP)

The nucleic acid sequence and deduced amino acid sequence of the base and second isoforms of the wild type chromoprotein hcFP640 (hcCP) are provided in FIGS. 1 and 2, respectively. The absorption spectra of the first base isoform wild type hcFP640 (hcCP) was measured using the protocol described in: Matz et al., Nature Biotech., 1999, 17: 969–973) and is provided in FIG. 3. An alternative embodiment of this chromoprotein is provided in FIG. 17.

II. Mutants

A. Generation of mutC148S

Upon alignment of the subject chromoprotein of SEQ ID NO:02 with GFP according to the protocol described in Matz et al., supra, residue 148 (numbering based on GFP) was identified as being occupied by a Cys residue instead of a Ser residue, where Ser 148 is present in all of the fluorescent Anthozoa derived proteins disclosed in the Matz et al., reference, supra. Site directed mutagenesis was employed to generate point mutants of the chromoprotein containing Ser at position 148. Mutagenesis was performed by the overlap extension method (Ho, S. N., Hunt, H. D., Horton, R. M., Pullen, J. K., Pease, L. R., 1989. Site-directed mutagenesis by overlap extension using the polymerase chain reaction. Gene 77, 51–59.). Briefly, two overlapping fragments of each FP coding region were amplified. "Forward cloning" (5'-acatggatccgctggtttgttgaaaga) (SEQ ID NO:19) and "reverse mutagenesis" (5'-acctcagtgcftggctccat) (SEQ ID NO:20) primers were used for 5'-end fragment amplification, and "forward mutagenesis" (5'-atgggagccaagcactgaggt) (SEQ ID NO:21) and "reverse cloning" (5'-tgacaagcttctggtgtcactgggaacaatca) (SEQ ID NO: 22) primers were used for 3'-end fragment amplification. PCR was carried out using Advantage® 2 Polymerase Mix (CLONTECH) in 1×manufacturer's buffer supplemented with 100 µM of each dNTP, 0.2 µM of each primer and 1 ng of plasmid DNA in 25 µl (final volume). The cycling parameters were set at: 95° C. for 10 s, 65° C. for 30 s, 72° C. for 30 s. 20 cycles were completed using PTC-200 MJ Research Thermocycler. To remove plasmids encoding wild type proteins, the 5'- and 3'-fragments were excised from 2% low-melting agarose gel in 1×TAE buffer. To drain the DNA solution, the gel pieces were subjected to 3 freeze-thaw cycles. Then, 5'- and 3'-fragments were combined to obtain full-length cDNA as follows. Equal volumes of 5'-fragment solution, 3'-fragment solution and 3×PCR mixture containing Advantage 2 Polymerase Mix, buffer and dNTPs were mixed together and subjected to 2–3 cycles of 95° C. for 20 s, 65° C. for 30 min, 72° s. Then, the reaction was diluted 10 fold and 1 µl of the diluted sample was used as a template for PCR with forward and reverse cloning primers (as described above for 5'- and 3'-fragments amplification). As a result, ready-for-cloning fragment containing full-length coding regions with target substitution was generated. This single substitution dramatically increased the quantum yield of red fluorescence as compared to the wild type protein. After that, by means of random mutagenesis of the primary fluorescent mutant (with Ser148), a brighter mutant, i.e., 44-9 (hcFRFP) (HcRed), was generated.

B. Characterization of Fluorescent Mutants 1. mutC148S

The nucleic acid sequence and deduced amino acid sequence of mutC148S are provided in FIG. 4, SEQ ID NOS. 05 and 06, respectively. The absorption spectra of mutC148S was measured using the protocol described above and is provided in FIG. 3. The excitation and emission spectra of mutC148S was measured using the protocol describe in: Matz et al., Nature Biotech., 1999,17: 969–973) and is provided in FIGS. 5A and 5B. An alternative embodiment of this mutant is provided in FIG. 15 (SEQ ID NOs. 23 and 24)

2. mut44-9 (hcFRFP) (HcRed)

mut 44-9 (hcFRFP) (HcRed) differs from the wild type chromoprotein as follows (where numbering is with respect to GFP according to the protocol described in Matz et al., supra): A5S; T39A; C148S; L181H; P208L; K211E. (Using self numbering, this mutant differs from wild type as follows: A2S, T36A, C143S, L173H, P201L, K204E)

The nucleic acid sequence and deduced amino acid sequence of mut44-9 is provided in FIG. 6, SEQ ID NOS. 07 and 08, respectively. The excitation and emission spectra of mut44-9 was measured using the protocol describe in: Matz et al., Nature Biotech., 1999, 17: 969–973) and is provided in FIGS. 7A and 7B.

3. mut 44-6 (*Crispa* 44-6)

This mutant possesses the following six amino acid substitutions vs. wild type: A2S, T36A, E63A, C143S, L173H, P201L (self-numbering). (for GEP numbering. See e.g., Matz et al., supra.) The amino acid sequence of this mutant is provided in FIG. 8 (SEQ ID NO. 10) and the nucleic acid coding sequence therefore is provided in FIG. 8 (SEQ ID NO:09). The excitation and emission spectra of mut44-6 was measured using the protocol describe in: Matz et al., Nature Biotech., 1999, 17: 969–973) and is provided in FIG. 9. An alternative embodiment of this mutant is provided in FIG. 16 (SEQ ID Nos. 25 and 26).

4. FP10-cr1 (hcFRFP-2) (HcRed-2A)

FP10-cr1 was generated based on mutant "44-9" by introducing one (three) substitutions—L 126(122)H R176 (168)H, E211(204)K In comparison with the wild type protein, FP10-cr1 carries the following substitutions:

A5S, T39A, L126H, C148S, L181H, R176H; P208L according to GFP numbering, describe in Matz et al., supra A2S, T36A, L122H, C143S, R168H L173H, P201L according to self-numbering The amino acid sequence (SEQ ID NO:12) and a nucleic acid encoding sequence therefore (SEQ ID NO:11) are provided in FIG. 10. (Also shown are sequences of alternative embodiments of this mutant, i.e., SEQ ID NOs: 13 and 14).

This mutant has a far red-shifted wavelength that provides for excellent multiplexing use with other NFPs. The excitation and emission spectra of mut44-6 was measured using the protocol describe in: Matz et al., Nature Biotech., 1999, 17: 969–973 and is provided in FIG. 11.

This mutant has been observed to form dimers as opposed to tetramers under physiologic conditions, as described in greater detail below.

5. hc-4

In comparison with the wild type protein, hc-4 carries the following substitutions:

A5S, C148S, P208L, according to GFP numbering, describe in Matz et al., supra

This mutant possesses similar spectral characteristics to its parental C148S mutant, but is not temperature sensitive, attaining maximum brightness after overnight growth at 37° C. in *E.Coli*.

6. hc-44

In comparison with the wild type protein, hc-44 carries the following substitutions:

A5S, T39A, C148S, L181H, P208L, according to GFP numbering, describe in Matz et al., supra This mutant was 3-fold brighter than hc-4, and displayed slightly more red-shifted fluorescence that peaked at 645 nm.

7. hc-41

In comparison with the wild type protein, hc-41 carries the following substitutions:

A5S, T39A, L126H, C148S, L181H, P208L, K211E according to GFP numbering, described in Matz et al., supra This mutant is a dimeric mutant of the wild type tetrameric protein. It is believed that the L126H mutation specifically imparts the dimeric phenotype to this mutant.

III. Characterization of Specific Mutants

A. Mut 44-9 (hcFRFP) (HcRed)

An equivalent comparison of *E. coli* colonies expressing drFP583 and hcFRFP (HcRed) HcRed under the fluorescence microscope reveals a marked difference between the orange color of drFP583 and the truly red color of HcRed. Additionally, HcRed maturates more rapidly than drFP583, as confirmed by the brighter fluorescence displayed by colonies containing the former protein after overnight expression in *E. coli*. However, it must be noted that the ultimate fluorescence intensity of mature drFP583 is considerably higher (about fivefold) than that of HcRed.

Spectral properties of HcRed (excitation maximum at 592 nm, emission maximum at 645 nm) make it suitable for FACS analysis with the 600 nm dye-laser. HEK 293 cells transfected with drFP583 were readily detected with a 488-nm argon ion laser (PE channel), but not with a 600-nm dye laser. Conversely, HcRed-transfected cells displayed no fluorescence when excited at 488 nm, but were clearly visible with the 600-nm laser (TxRed and APC channels). Our data indicate that the mutant HcRed may be employed for additional far-red color in multi-color flow cytometry applications.

B. Oligomerization Studies

We tested the oligomeric state of the certain of the above novel fluorescent proteins by gel filtration analysis, using EGFP (enhanced green fluorescent protein) and drFP583 as monomer and tetramer standards, respectively. A dimeric mutant of the wild type chromoprotein hcCP (denoted hc-41) was detected, which migrated between EGFP and drFP583. This protein contained eight amino acid substitutions, specifically, A5S, S43G, E65A, L126H, K141E, C148S, R186K and P208L (as described above). Within these substitutions, only one mutation, L126H, may be responsible for modifying the oligomeric state of the protein, since the Ile residue at this position participates in formation of the tetrameric interface in drFP583. As hc-41 possessed relatively blue-shifted fluorescence (emission $_{Ima}X$=625 nm), we introduced the L126H mutation into HcRed. The resultant mutant was designated HcRed-2. Gel-filtration analyses revealed the dimeric nature of this protein. Following random mutagenesis of HcRed-2 resulted in brighter dimeric variant HcRed-2A (also referred to above as cr-1) containing two additional amino acid substitutions, specifically, R176H and E211K (according to GFP numbering). Spectral and maturation properties of HcRed-2A were similar to those of HcRed. *E. coli*-expressed HcRed-2A maturated nearly completely during overnight growth and displayed excitation and emission maxima at 590 and 640 nm, respectively. In certain embodiments, the dimeric HcRed-2 is more suitable than tetrameric drFP583 for functional fusion protein construction.

C. Fusion Constructs

A Cr-44-9-tandem (linked dimer), and a Cr-449-tandem-actin fusion were constructed. The amino acid sequence and encoding nucleotide sequence for the Cr-44-9 tandem fusion protein are provided in FIG. 12, as SEQ ID NOs 15 & 16. The amino acid and encoding nucleotide sequence for the Cr-44-9 tandem-actin fusion protein are provided in FIG. 13, as SEQ ID NOs. 17 & 18). The above constructs were expressed in mammalian cells, and the encoded fluorescent proteins were detectable.

D. FIGS. 14A to F show the results of Flow cytometry analysis of HEK 293 cells transfected with Cr-449 (C, D), DsRed (E, F) or mock transfected (A, B) 48 hours post-transfection. The 488-nm laser was used in panels A, C, E and 600-nm laser was used in panels B, D, F. Contour plots (5% probability with outliners) are shown. Dead cells were excluded from analysis. Standard compensations and filter sets for Vanford FACS machine were used.

IV. Summary

| | | SPECTRAL PROPERTIES | | | | |
|---|---|---|---|---|---|---|
| Species | nFP Name | Absorbance Maximum nm | Emission Maximum nm | Maximum Extinction Coeff. | Quantum Yield | Relative Brightness* |
| *Heteractis* 'base isoform' | HcFP640 hcCP Wild Type | 577 | 640 | 59,200 | 0.000 | 0.001 |
| *Heteractis* | Mut C148S | 577 | 640 | 56,100 | 0.007 | 0.018 |
| *Heteractis* | Mut 44-9 | 591 | 645 | 29,200 | 0.042 | 0.055 |

*relative brightness is extinction coefficient multiplied by quantum yield divided by the same value for A. victoria GFP.

It is evident from the above discussion and results that the subject invention provides important new chromoproteins and fluorescent proteins and nucleic acids encoding the same. A particularly important advantage provided by the subject invention is a far red shifted fluorescent protein. The subject proteins and nucleic acids find use in a variety of different applications. As such, the subject invention represents a significant contribution to the art.

All publications and patent applications cited in this specification are herein incorporated by reference as if each individual publication or patent application were specifically and individually indicated to be incorporated by reference.

The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A nucleic acid present in other than its natural environment, wherein said nucleic acid encodes a far red shifted Stichodactylidaen chromoprotein or fluorescent mutant thereof, and wherein said nucleic acid has a sequence identity of at least about 95% with SEQ ID NO: 11.

2. The nucleic acid according to claim 1, wherein said nucleic acid is isolated.

3. A nucleic acid present in other than its natural environment, wherein said nucleic acid encodes a fluorescent Stichodactylidaen protein having an emission maximum ranging from 620 to 680 nm.

4. The nucleic acid according to claim 3, wherein said nucleic acid is isolated.

5. The nucleic acid according to claim 1, wherein said nucleic acid has the sequence of SEQ ID NO: 11.

6. A nucleic acid present in other than its natural environment that encodes fluorescent protein having an emission maximum ranging from 620 to 680 nm and having a sequence identity of at least about 95% with SEQ ID NO: 11.

7. An isolated nucleic acid that hybridizes under stringent conditions to a nucleic acid selected from the group consisting of:
   (a) a nucleic acid that encodes a fluorescent Stichodactylidaen protein having an emission maximum ranging from 620 to 680 nm; and
   (b) a nucleic acid having a sequence identity of at least about 95% with SEQ ID NO: 11 that encodes a fluorescent protein;
      or its complementary sequence, wherein said stringent conditions are at least as stringent as hybridization at 42° C. in a solution comprising 50% formamide, 5×SSC, 50 mM sodium phosphate, 5× Denhardt's solution, and 10% dextran sulfate followed by washing the filters in 0.1×SSC at about 650° C.

8. A construct comprising a vector and a nucleic acid selected from the group consisting of:
   (a) a nucleic acid that encodes a fluorescent Stichodactylidaen protein having an emission maximum ranging from 620 to 680 nm; and
   (b) a nucleic acid having a sequence identity of at least about 95% with SEQ ID NO: 11.

9. An expression cassette comprising:
   (a) a transcriptional initiation region functional in an expression host;
   (b) a nucleic acid selected from the group consisting of the nucleic acids of:
      (i) a nucleic acid that encodes a fluorescent Stichodactylidaen protein having an emission maximum ranging from 620 to 680 nm; and
      (ii) a nucleic acid having a sequence identity of at least about 95% with SEQ ID NO: 11 that encodes a fluorescent protein; and
   (c) and a transcriptional termination region functional in said expression host.

10. A cell, or the progeny thereof, comprising an expression cassette according to claim 9 as part of an extrachromosomal element or integrated into the genome of a host cell as a result of introduction of said expression cassette into said host cell.

11. A method of producing a Stichodactylidaen chromo and/or fluorescent protein, said method comprising:
   growing a cell according to claim 10, whereby said protein is expressed; and
   isolating said protein substantially free of other proteins.

12. In an application that employs a nucleic acid encoding a chromo- or fluorescent protein, the improvement comprising:
   employing a nucleic acid selected from the group consisting of:
      (i) a nucleic acid that encodes a fluorescent Stichodactylidaen protein having an emission maximum ranging from 620 to 680 nm; and
      (ii) a nucleic acid having a sequence identity of at least about 95% with SEQ ID NO: 11.

13. A kit comprising:
   a nucleic acid selected from the group consisting of:
      (i) a nucleic acid that encodes a fluorescent Stichodactylidaen protein having an emission maximum ranging from 620 to 680 nm; and
      (ii) a nucleic acid having a sequence identity of at least about 95% with SEQ ID NO: 11 that encodes a fluorescent protein; and
   instructions for using said nucleic acid.

14. A nucleic acid present in other than its natural environment that encodes fluorescent protein wherein said nucleic acid has a sequence identity of at least about 95% with SEQ ID NO: 11.

15. An isolated nucleic acid-that hybridizes under stringent conditions to a nucleic acid that encodes a fluorescent protein wherein said nucleic acid has a sequence identity of at least about 95% with SEQ ID NO: 11 that encodes a fluorescent protein;
   or its complementary sequence, wherein said stringent conditions are at least as stringent as hybridization at 42° C. in a solution comprising 50% formamide, 5×SSC, 50 mM sodium phosphate, 5× Denhardt'solution, and 10% dextran sulfate followed by washing the filters in 0.1× SSC at about 65° C.

16. A construct comprising a vector and a nucleic acid, wherein said nucleic acid has a sequence identity of at least about 95% with SEQ ID NO: 11.

17. An expression cassette comprising:
   (a) a transcriptional initiation region functional in an expression host;
   (b) a nucleic acid having a sequence identity of at least about 95% with SEQ ID NO: 11 that encodes a fluorescent protein; and
   (c) and a transcriptional termination region functional in said expression host.

18. In an application that employs a nucleic acid encoding a chromo- or fluorescent protein, the improvement comprising:
employing a nucleic acid, wherein said nucleic acid has a sequence identity of at least about 95% with SEQ ID NO:11.

19. The nucleic acid according to claim 1, wherein said protein has one or more amino acid substitutions at positions 2, 36, 63, 143, 173, 201 and 204 as compared to the wild type sequence comprising the amino acid sequence of SEQ ID NO: 2.

20. The nucleic acid according to claim 1, wherein said protein has one or more amino acid substitutions at positions A2S, T36A, E63A, C143S, L173H, P201L and K204E as compared to the wild type sequence comprising the amino acid sequence of SEQ ID NO: 2.

21. The nucleic acid according to claim 6, wherein said protein has one or more amino acid substitutions at positions 2, 36, 63,143,173, 201 and 204 as compared to the wild type sequence comprising the amino acid sequence of SEQ ID NO: 2.

22. The nucleic acid according to claim 6, wherein said protein has one or more amino acid substitutions at positions A2S, T36A, E63A, C143S, L173H, P201L and K204E as compared to the wild type sequence comprising the amino acid sequence of SEQ ID NO: 2.

* * * * *

UNITED STATES PATENT AND TRADEMARK OFFICE
CERTIFICATE OF CORRECTION

PATENT NO. : 7,157,565 B2 Page 1 of 1
APPLICATION NO. : 09/976673
DATED : January 2, 2007
INVENTOR(S) : Sergey Lukyanov et al.

It is certified that error appears in the above-identified patent and that said Letters Patent is hereby corrected as shown below:

Column 59, Line 27, please change as follows: ~~encodes fluorescent~~ encodes a fluorescent

Column 59, Line 43, please change as follows: 42° C[[.]] in 42° C in

Column 59, Line 46, please change as follows: about 65[[0]]° C. about 65° C.

Column 60, Line 42, please change as follows: ~~encodes fluorescent~~ encodes a fluorescent

Column 60, Line 53, please change as follows: 42° C[[.]] in 42° C in

Signed and Sealed this

Twenty-ninth Day of January, 2008

JON W. DUDAS
*Director of the United States Patent and Trademark Office*

SEQUENCE LISTING

```
<160> NUMBER OF SEQ ID NOS: 26

<210> SEQ ID NO 1
<211> LENGTH: 910
<212> TYPE: DNA
<213> ORGANISM: heteractis crispa

<400> SEQUENCE: 1
accatttgct ttggttcctt ggcaaacgaa agtttagaac gaaaactgac ccaaattaca      60
tcttcctcct ggatccttac catggctggt ttgttgaaag aaagtatgcg catcaagatg     120
tacatggaag gcacggttaa tggccattat ttcaagtgtg aaggagaggg agacggcaac     180
ccatttacag gtacgcagag catgaggatt catgtcaccg aagggctcc  attaccattt     240 gccttcgaca ttttggcacc gtgttgtgag tacggcagca ggacctttgt ccaccatacg     300
gcagagattc ccgatttctt caagcagtct ttccctgaag gctttacttg ggaaagaacc     360
acaacctatg aagatggagg cattcttact gctcatcagg acacaagcct ggaggggaac     420
tgccttatat acaaggtgaa agtccttggt accaattttc ctgctgatgg ccccgtgatg     480
aagaacaaat caggaggatg ggagccatgc actgaggtgg tttatccaga gaatggtgtc     540
ctgtgtggac gtaatgtgat ggcccttaaa gtcggtgatc gtcgtttgat ctgccatctc     600
tatacttctt acaggtccaa gaaagcagtc cgtgccttga caatgccagg atttcatttt     660
acagacatcc gccttcagat gccgaggaaa acgaaagacg agtactttga actgtacgaa     720
gcatctgtgg ctaggtacag tgatcttcct gaaaaagcaa attgattgtt cccagtgaca     780
ccagactgct gtcagctttt ggttaaagcc cgaaagacaa aaggacattt gtagtttagt     840
```

```
ttatatttcc ctttcatttg tgaatcaaca ttgtactctc tgtaaacctt taaaatgctc    900
cattaaacct                                                           910
```

<210> SEQ ID NO 2
<211> LENGTH: 227
<212> TYPE: PRT
<213> ORGANISM: heteractis crispa

<400> SEQUENCE: 2

```
Met Ala Gly Leu Leu Lys Glu Ser Met Arg Ile Lys Met Tyr Met Glu
 1               5                  10                  15

Gly Thr Val Asn Gly His Tyr Phe Lys Cys Glu Gly Glu Gly Asp Gly
             20                  25                  30

Asn Pro Phe Thr Gly Thr Gln Ser Met Arg Ile His Val Thr Glu Gly
         35                  40                  45

Ala Pro Leu Pro Phe Ala Phe Asp Ile Leu Ala Pro Cys Cys Glu Tyr
     50                  55                  60

Gly Ser Arg Thr Phe Val His His Thr Ala Glu Ile Pro Asp Phe Phe
 65                  70                  75                  80

Lys Gln Ser Phe Pro Glu Gly Phe Thr Trp Glu Arg Thr Thr Thr Tyr
                 85                  90                  95

Glu Asp Gly Gly Ile Leu Thr Ala His Gln Asp Thr Ser Leu Glu Gly
            100                 105                 110

Asn Cys Leu Ile Tyr Lys Val Lys Val Leu Gly Thr Asn Phe Pro Ala
        115                 120                 125

Asp Gly Pro Val Met Lys Asn Lys Ser Gly Gly Trp Glu Pro Cys Thr
    130                 135                 140

Glu Val Val Tyr Pro Glu Asn Gly Val Leu Cys Gly Arg Asn Val Met
145                 150                 155                 160

Ala Leu Lys Val Gly Asp Arg Arg Leu Ile Cys His Leu Tyr Thr Ser
                165                 170                 175

Tyr Arg Ser Lys Lys Ala Val Arg Ala Leu Thr Met Pro Gly Phe His
            180                 185                 190

Phe Thr Asp Ile Arg Leu Gln Met Pro Arg Lys Thr Lys Asp Glu Tyr
        195                 200                 205

Phe Glu Leu Tyr Glu Ala Ser Val Ala Arg Tyr Ser Asp Leu Pro Glu
    210                 215                 220

Lys Ala Asn
225
```

<210> SEQ ID NO 3
<211> LENGTH: 908
<212> TYPE: DNA
<213> ORGANISM: heteractis crispa

<400> SEQUENCE: 3

```
accatttgct ttggttcctt ggcaaacgaa agtttagacg aaaactgacc caaattacat     60
cctcctgatc cttaccatgg ctggtttgtt gaaagaaagt atgcgcatca agatgtacat    120
ggaaggcacg gttaatggcc attatttcaa gtgtgaagga gagggagacg gcaacccatt    180
tacaggtacg cagagcatga ggattcatgt caccgaaggg gctccattac catttgcctt    240
cgacattttg gcaccgtgtt gtgagtacgg cagcaggacc tttgtccacc atacggcaga    300
gattcccgat tcttcaagc agtctttccc tgaaggcttt acttgggaa gaaccacaac     360 ctatgaagat ggaggcattc ttactgctca tcaggacaca agcctggagg ggaactgcct    420
```

```
tatatacaag gtgaaagtcc ttggtaccaa ttttcctgct gatggcyccg tgatgaagaa    480
caaatcagaa ggatgggagc catgcactga ggtggtttat ccagataatg gtgtcctgtg    540
tggacgtaat gtgatggccc ttaaagtcgg tgatcgtcgt ttgatctgcc atctctatac    600
ttcttacagg tccaagaaag cagtccgtgc cttgacaatg ccaggatttc attttacaga    660
catccgcctt cagatgccga ggaaaacgaa agacgagtac tttgaactgt acgaagcatc    720
tgtggctagg tacagtgatc ttcctgaaaa agcaaattga ttgttcccag tgacaccaga    780
ctgctgtcag cttttggtta aagcccgaaa gacaaaagga catttgtagt tttagtttat    840 attttcccctt tcattttgtg aatcaacatt gtactctctg taaacctttta aaatgctcca    900 ttaaacct                                                             908
```

<210> SEQ ID NO 4
<211> LENGTH: 227
<212> TYPE: PRT
<213> ORGANISM: heteractis crispa

<400> SEQUENCE: 4

```
Met Ala Gly Leu Leu Lys Glu Ser Met Arg Ile Lys Met Tyr Met Glu
 1               5                  10                  15

Gly Thr Val Asn Gly His Tyr Phe Lys Cys Glu Gly Glu Gly Asp Gly
             20                  25                  30

Asn Pro Phe Thr Gly Thr Gln Ser Met Arg Ile His Val Thr Glu Gly
         35                  40                  45

Ala Pro Leu Pro Phe Ala Phe Asp Ile Leu Ala Pro Cys Cys Glu Tyr
     50                  55                  60

Gly Ser Arg Thr Phe Val His His Thr Ala Glu Ile Pro Asp Phe Phe
 65                  70                  75                  80

Lys Gln Ser Phe Pro Glu Gly Phe Thr Trp Glu Arg Thr Thr Thr Tyr
                 85                  90                  95

Glu Asp Gly Gly Ile Leu Thr Ala His Gln Asp Thr Ser Leu Glu Gly
            100                 105                 110

Asn Cys Leu Ile Tyr Lys Val Lys Val Leu Gly Thr Asn Phe Pro Ala
        115                 120                 125

Asp Gly Pro Val Met Lys Asn Lys Ser Glu Gly Trp Glu Pro Cys Thr
    130                 135                 140

Glu Val Val Tyr Pro Asp Asn Gly Val Leu Cys Gly Arg Asn Val Met
145                 150                 155                 160

Ala Leu Lys Val Gly Asp Arg Arg Leu Ile Cys His Leu Tyr Thr Ser
                165                 170                 175

Tyr Arg Ser Lys Lys Ala Val Arg Ala Leu Thr Met Pro Gly Phe His
            180                 185                 190

Phe Thr Asp Ile Arg Leu Gln Met Pro Arg Lys Thr Lys Asp Glu Tyr
        195                 200                 205

Phe Glu Leu Tyr Glu Ala Ser Val Ala Arg Tyr Ser Asp Leu Pro Glu
    210                 215                 220

Lys Ala Asn
225
```

<210> SEQ ID NO 5
<211> LENGTH: 684
<212> TYPE: DNA
<213> ORGANISM: heteractis crispa

```
<400> SEQUENCE: 5
atggctggtt tgttgaaaga agtatgcgc atcaagatgt acatggaagg cacggttaat      60
ggccattatt tcaagtgtga aggagaggga gacggcaacc catttacagg tacgcagagc    120
atgaggattc atgtcaccga agggctcca ttaccatttg ccttcgacat tttggcaccg     180
tgttgtgagt acggcagcag gaccttttgtc caccataccgg cagagattcc cgatttcttc   240
aagcagtctt tccctgaagg ctttacttgg aaagaaccaa caacctatga agatggaggc    300
attcttactg ctcatcagga cacaagcctg gagggaact gccttatata caaggtgaaa    360
gtccttggta ccaattttcc tgctgatggc cccgtgatga gaacaaatc aggaggatgg    420 gagccaagca ctgaggtggt ttatccagag aatggtgtcc tgtgtggacg taatgtgatg    480
gcccttaaag tcggtgatcg tcgtttgatc tgccatctct atacttctta caggtccaag   540
aaagcagtcc gtgccttgac aatgccagga tttcatttta cagacatccg ccttcagatg   600
ccgaggaaaa cgaaagacga gtactttgaa ctgtacgaag catctgtggc taggtacagt   660
gatcttcctg aaaaagcaaa ttga                                           684

<210> SEQ ID NO 6
<211> LENGTH: 227
<212> TYPE: PRT
<213> ORGANISM: heteractis crispa

<400> SEQUENCE: 6

Met Ala Gly Leu Leu Lys Glu Ser Met Arg Ile Lys Met Tyr Met Glu
  1               5                  10                  15

Gly Thr Val Asn Gly His Tyr Phe Lys Cys Glu Gly Glu Gly Asp Gly
                 20                  25                  30

Asn Pro Phe Thr Gly Thr Gln Ser Met Arg Ile His Val Thr Glu Gly
             35                  40                  45

Ala Pro Leu Pro Phe Ala Phe Asp Ile Leu Ala Pro Cys Cys Glu Tyr
         50                  55                  60

Gly Ser Arg Thr Phe Val His His Thr Ala Glu Ile Pro Asp Phe Phe
 65                  70                  75                  80

Lys Gln Ser Phe Pro Glu Gly Phe Thr Trp Glu Arg Thr Thr Thr Tyr
                 85                  90                  95

Glu Asp Gly Gly Ile Leu Thr Ala His Gln Asp Thr Ser Leu Glu Gly
                100                 105                 110

Asn Cys Leu Ile Tyr Lys Val Lys Val Leu Gly Thr Asn Phe Pro Ala
            115                 120                 125

Asp Gly Pro Val Met Lys Asn Lys Ser Gly Gly Trp Glu Pro Ser Thr
        130                 135                 140

Glu Val Val Tyr Pro Glu Asn Gly Val Leu Cys Gly Arg Asn Val Met
145                 150                 155                 160

Ala Leu Lys Val Gly Asp Arg Arg Leu Ile Cys His Leu Tyr Thr Ser
                165                 170                 175

Tyr Arg Ser Lys Lys Ala Val Arg Ala Leu Thr Met Pro Gly Phe His
            180                 185                 190

Phe Thr Asp Ile Arg Leu Gln Met Pro Arg Lys Thr Lys Asp Glu Tyr
        195                 200                 205

Phe Glu Leu Tyr Glu Ala Ser Val Ala Arg Tyr Ser Asp Leu Pro Glu
    210                 215                 220

Lys Ala Asn
225
```

<210> SEQ ID NO 7
<211> LENGTH: 681
<212> TYPE: DNA
<213> ORGANISM: heteractis crispa

<400> SEQUENCE: 7

```
tctggtttgt tgaaagaaag tatgcgcatc aagatgtaca tggaaggcac ggttaatggc      60
cattatttca agtgtgaagg agagggagac ggcaacccat ttgcaggtac gcagagcatg     120
aggattcatg tcaccgaagg ggctccatta ccatttgcct tcgacatttt ggcaccgtgt     180
tgtgagtacg gcagcaggac ctttgtccac catacggcag agattcccga tttcttcaag     240
cagtctttcc ctgaaggctt tacttgggaa agaaccacaa cctatgaaga tggaggcatt     300
cttactgctc atcaggacac aagcctggag gggaactgcc ttatatacaa ggtgaaagtc     360
cttggtacca attttcctgc tgatggcccc gtgatgaaga caaatcagg aggatgggag      420
ccaagcactg aggtggttta tccagagaat ggtgtcctgt gtggacgtaa tgtgatggcc     480
cttaaagtcg gtgatcgtcg tttgatctgc catcactata cttcttacag gtccaagaaa     540
gcagtccgtg ccttgacaat gccaggattt cattttacag acatccgcct tcagatgctg     600
aggaaagaga agacgagta cttttgaactg tacgaagcat ctgtggctag gtacagtgat     660
cttcctgaaa agcaaattg a                                                681
```

<210> SEQ ID NO 8
<211> LENGTH: 226
<212> TYPE: PRT
<213> ORGANISM: heteractis crispa

<400> SEQUENCE: 8

```
Ser Gly Leu Leu Lys Glu Ser Met Arg Ile Lys Met Tyr Met Glu Gly
  1               5                  10                  15
Thr Val Asn Gly His Tyr Phe Lys Cys Glu Gly Glu Gly Asp Gly Asn
             20                  25                  30
Pro Phe Ala Gly Thr Gln Ser Met Arg Ile His Val Thr Glu Gly Ala
         35                  40                  45
Pro Leu Pro Phe Ala Phe Asp Ile Leu Ala Pro Cys Cys Glu Tyr Gly
     50                  55                  60
Ser Arg Thr Phe Val His His Thr Ala Glu Ile Pro Asp Phe Phe Lys
 65                  70                  75                  80
Gln Ser Phe Pro Glu Gly Phe Thr Trp Glu Arg Thr Thr Thr Tyr Glu
                 85                  90                  95
Asp Gly Gly Ile Leu Thr Ala His Gln Asp Thr Ser Leu Glu Gly Asn
            100                 105                 110
Cys Leu Ile Tyr Lys Val Lys Val Leu Gly Thr Asn Phe Pro Ala Asp
        115                 120                 125
Gly Pro Val Met Lys Asn Lys Ser Gly Gly Trp Glu Pro Ser Thr Glu
    130                 135                 140
Val Val Tyr Pro Glu Asn Gly Val Leu Cys Gly Arg Asn Val Met Ala
145                 150                 155                 160
Leu Lys Val Gly Asp Arg Arg Leu Ile Cys His His Tyr Thr Ser Tyr
                165                 170                 175
Arg Ser Lys Lys Ala Val Arg Ala Leu Thr Met Pro Gly Phe His Phe
            180                 185                 190
Thr Asp Ile Arg Leu Gln Met Leu Arg Lys Glu Lys Asp Glu Tyr Phe
        195                 200                 205
```

```
Glu Leu Tyr Glu Ala Ser Val Ala Arg Tyr Ser Asp Leu Pro Glu Lys
    210                 215                 220

Ala Asn
225

<210> SEQ ID NO 9
<211> LENGTH: 681
<212> TYPE: DNA
<213> ORGANISM: heteractis crispa

<400> SEQUENCE: 9
tctggtttgt tgaaagaaag tatgcgcatc aagatgtaca tggaaggcac ggttaatggc      60
cattatttca agtgtgaagg agagggagac ggcaacccat ttgcaggtac gcagagcatg     120
aggattcatg tcaccgaagg ggctccatta ccatttgcct tcgacatttt ggcaccgtgt     180
tgtgcgtacg gcagcaggac ctttgtccac catacggcag agattcccga tttcttcaag     240
cagtctttcc ctgaaggctt tacttgggaa agaaccacaa cctatgaaga tggaggcatt     300
cttactgctc atcaggacac aagcctggag gggaactgcc ttatatacaa ggtgaaagtc     360
cttggtacca atttttcctgc tgatggcccc gtgatgaaga acaaatcagg aggatgggag     420
ccaagcactg aggtggttta tccagagaat ggtgtcctgt gtggacgtaa tgtgatggcc     480
cttaaagtcg gtgatcgtcg tttgatctgc atcactata cttcttacag gtccaagaaa     540
gcagtccgtg ccttgacaat gccaggattt catttacag acatccgcct tcagatgctg     600
aggaaagaga aagacgagta ctttgaactg tacgaagcat ctgtggctag gtacagtgat     660
cttcctgaaa agcaaattg a                                                681

<210> SEQ ID NO 10
<211> LENGTH: 226
<212> TYPE: PRT
<213> ORGANISM: heteractis crispa

<400> SEQUENCE: 10

Ser Gly Leu Leu Lys Glu Ser Met Arg Ile Lys Met Tyr Met Glu Gly
  1               5                  10                  15

Thr Val Asn Gly His Tyr Phe Lys Cys Glu Gly Glu Gly Asp Gly Asn
             20                  25                  30

Pro Phe Ala Gly Thr Gln Ser Met Arg Ile His Val Thr Glu Gly Ala
         35                  40                  45

Pro Leu Pro Phe Ala Phe Asp Ile Leu Ala Pro Cys Cys Ala Tyr Gly
     50                  55                  60

Ser Arg Thr Phe Val His His Thr Ala Glu Ile Pro Asp Phe Phe Lys
 65                  70                  75                  80

Gln Ser Phe Pro Glu Gly Phe Thr Trp Glu Arg Thr Thr Thr Tyr Glu
                 85                  90                  95

Asp Gly Gly Ile Leu Thr Ala His Gln Asp Thr Ser Leu Glu Gly Asn
            100                 105                 110

Cys Leu Ile Tyr Lys Val Lys Val Leu Gly Thr Asn Phe Pro Ala Asp
        115                 120                 125

Gly Pro Val Met Lys Asn Lys Ser Gly Gly Trp Glu Pro Ser Thr Glu
    130                 135                 140

Val Val Tyr Pro Glu Asn Gly Val Leu Cys Gly Arg Asn Val Met Ala
145                 150                 155                 160

Leu Lys Val Gly Asp Arg Arg Leu Ile Cys His His Tyr Thr Ser Tyr
                165                 170                 175
```

-continued

```
Arg Ser Lys Lys Ala Val Arg Ala Leu Thr Met Pro Gly Phe His Phe
            180                 185                 190
Thr Asp Ile Arg Leu Gln Met Leu Arg Lys Glu Lys Asp Glu Tyr Phe
        195                 200                 205
Glu Leu Tyr Glu Ala Ser Val Ala Arg Tyr Ser Asp Leu Pro Glu Lys
    210                 215                 220
Ala Asn
225
```

<210> SEQ ID NO 11
<211> LENGTH: 687
<212> TYPE: DNA
<213> ORGANISM: heteractis crispa

<400> SEQUENCE: 11

```
atggtgagcg gcctgctgaa ggagagtatg cgcatcaaga tgtacatgga gggcaccgtg      60
aacggccact acttcaagtg cgagggcgag ggcgacggca ccccttcgc cggcacccag     120
agcatgagaa tccacgtgac cgagggcgcc cccctgccct tcgccttcga catcctggcc    180
ccctgctgcg agtacggcag caggaccttc gtgcaccaca ccgccgagat ccccgacttc    240
ttcaagcaga gcttccccga gggcttcacc tgggagagaa ccaccaccta cgaggacggc    300
ggcatcctga ccgcccacca ggacaccagc ctggagggca ctgcctgat ctacaaggtg     360
aaggtgcacg gcaccaactt ccccgccgac ggccccgtga tgaagaacaa gagcggcggc    420
tgggagccca gcaccgaggt ggtgtacccc gagaacggcg tgctgtgcgg ccggaacgtg    480
atggccctga aggtgggcga ccggcacctg atctgccacc actacaccag ctaccggagc    540
aagaaggccg tgcgcgccct gaccatgccc ggcttccact tcaccgacat ccggctccag    600
atgctgcgga agaagaagga cgagtacttc gagctgtacg aggccagcgt ggcccggtac    660
agcgacctgc ccgagaaggc caactga                                        687
```

<210> SEQ ID NO 12
<211> LENGTH: 227
<212> TYPE: PRT
<213> ORGANISM: heteractis crispa

<400> SEQUENCE: 12

```
Met Ser Gly Leu Leu Lys Glu Ser Met Arg Ile Lys Met Tyr Met Glu
  1               5                  10                  15
Gly Thr Val Asn Gly His Tyr Phe Lys Cys Glu Gly Glu Gly Asp Gly
             20                  25                  30
Asn Pro Phe Ala Gly Thr Gln Ser Met Arg Ile His Val Thr Glu Gly
         35                  40                  45
Ala Pro Leu Pro Phe Ala Phe Asp Ile Leu Ala Pro Cys Cys Glu Tyr
     50                  55                  60
Gly Ser Arg Thr Phe Val His His Thr Ala Glu Ile Pro Asp Phe Phe
 65                  70                  75                  80
Lys Gln Ser Phe Pro Glu Gly Phe Thr Trp Glu Arg Thr Thr Thr Tyr
                 85                  90                  95
Glu Asp Gly Gly Ile Leu Thr Ala His Gln Asp Thr Ser Leu Glu Gly
            100                 105                 110
Asn Cys Leu Ile Tyr Lys Val Lys Val His Gly Thr Asn Phe Pro Ala
        115                 120                 125
Asp Gly Pro Val Met Lys Asn Lys Ser Gly Gly Trp Glu Pro Ser Thr
    130                 135                 140
```

Glu Val Val Tyr Pro Glu Asn Gly Val Leu Cys Gly Arg Asn Val Met
145                 150                 155                 160

Ala Leu Lys Val Gly Asp Arg His Leu Ile Cys His Tyr Thr Ser
            165                 170                 175

Tyr Arg Ser Lys Lys Ala Val Arg Ala Leu Thr Met Pro Gly Phe His
            180                 185                 190

Phe Thr Asp Ile Arg Leu Gln Met Leu Arg Lys Thr Lys Asp Glu Tyr
        195                 200                 205

Phe Glu Leu Tyr Glu Ala Ser Val Ala Arg Tyr Ser Asp Leu Pro Glu
    210                 215                 220

Lys Ala Asn
225

<210> SEQ ID NO 13
<211> LENGTH: 687
<212> TYPE: DNA
<213> ORGANISM: heteractis crispa

<400> SEQUENCE: 13
atggtgagcg gcctgctgaa ggagagcatg cgcatcaaga tgtacatgga gggcaccgtg        60
aacggccact acttcaagtg cgagggcgag ggcgacggca accccttcgc cggcacccag       120
agcatgcgga tccacgtgac cgagggcgcc cccctgccct tcgccttcga catcctggcc       180
ccctgctgcg agtacggcag caggaccttc gtgcaccaca ccgccgagat ccccgacttc       240
ttcaagcaga gcttccccga gggcttcacc tgggagagaa ccaccaccta cgaggacggc       300
ggcatcctga ccgcccacca ggacaccagc ctggagggca ctgcctgat ctacaaggtg        360 aaggtgctgg gcaccaactt ccccgccgac ggccccgtga tgaagaacaa gagcggcggc       420
tgggagccca gcaccgaggt ggtgtacccc gagaacggcg tgctgtgcgg ccggaacgtg       480
atggccctga aggtgggcga ccggcggctg atctgccacc actacaccag ctaccggagc       540
aagaaggccg tgcgggccct gaccatgccc ggcttccact tcaccgacat ccggctgcag       600
atgctgcgga aggagaagga cgagtacttc gagctgtacg aggccagcgt ggcccggtac       660
agcgacctgc ccgagaaggc caactga                                           687

<210> SEQ ID NO 14
<211> LENGTH: 227
<212> TYPE: PRT
<213> ORGANISM: heteractis crispa

<400> SEQUENCE: 14

Met Ser Gly Leu Leu Lys Glu Ser Met Arg Ile Lys Met Tyr Met Glu
1               5                   10                  15

Gly Thr Val Asn Gly His Tyr Phe Lys Cys Glu Gly Glu Gly Asp Gly
            20                  25                  30

Asn Pro Phe Ala Gly Thr Gln Ser Met Arg Ile His Val Thr Glu Gly
        35                  40                  45

Ala Pro Leu Pro Phe Ala Phe Asp Ile Leu Ala Pro Cys Cys Glu Tyr
    50                  55                  60

Gly Ser Arg Thr Phe Val His His Thr Ala Glu Ile Pro Asp Phe Phe
65                  70                  75                  80

Lys Gln Ser Phe Pro Glu Gly Phe Thr Trp Glu Arg Thr Thr Thr Tyr
                85                  90                  95

Glu Asp Gly Gly Ile Leu Thr Ala His Gln Asp Thr Ser Leu Glu Gly
            100                 105                 110

Asn Cys Leu Ile Tyr Lys Val Lys Val His Gly Thr Asn Phe Pro Ala
            115                 120                 125

Asp Gly Pro Val Met Lys Asn Lys Ser Gly Gly Trp Glu Pro Ser Thr
    130                 135                 140

Glu Val Val Tyr Pro Glu Asn Gly Val Leu Cys Gly Arg Asn Val Met
145                 150                 155                 160

Ala Leu Lys Val Gly Asp Arg Arg Leu Ile Cys His His Tyr Thr Ser
                165                 170                 175

Tyr Arg Ser Lys Lys Ala Val Arg Ala Leu Thr Met Pro Gly Phe His
            180                 185                 190

Phe Thr Asp Ile Arg Leu Gln Met Leu Arg Lys Glu Lys Asp Glu Tyr
        195                 200                 205

Phe Glu Leu Tyr Glu Ala Ser Val Ala Arg Tyr Ser Asp Leu Pro Glu
    210                 215                 220

Lys Ala Asn
225

<210> SEQ ID NO 15
<211> LENGTH: 1396
<212> TYPE: DNA
<213> ORGANISM: Artificial Sequence
<220> FEATURE:
<223> OTHER INFORMATION: fusion construct

<400> SEQUENCE: 15
accggtcgcc accatggtga gcggcctgct gaaggagagc atgcgcatca agatgtacat      60
ggagggcacc gtgaacggcc actacttcaa gtgcgagggc gagggcgacg gcaacccctt     120
cgccggcacc cagagcatgc ggatccacgt gaccgagggc gcccccctgc ccttcgcctt     180
cgacatcctg gcccctgct gcgagtacgg cagcaggacc ttcgtgcacc acaccgccga     240
gatccccgac ttcttcaagc agagcttccc cgagggcttc acctgggaga gaaccaccac     300
ctacgaggac ggcggcatcc tgaccgccca ccaggacacc agcctggagg caactgcct      360 gatctacaag gtgaaggtgc tgggcaccaa cttccccgcc gacggccccg tgatgaagaa     420
caagagcggc ggctgggagc ccagcaccga ggtggtgtac cccgagaacg gcgtgctgtg     480
cggccggaac gtgatggccc tgaaggtggg cgaccggcgg ctgatctgcc accactacac     540
cagctaccgg agcaagaagg ccgtgcgggc cctgaccatg cccggcttcc acttcaccga     600
catccggctg cagatgctgc ggaaggagaa ggacgagtac ttcgagctgt acgaggccag     660
cgtggcccgg tacagcgacc tgcccgagaa ggccaacaga tctcccggga tggtgagcgg     720
cctgctgaag gagagcatgc gcatcaagat gtacatggag gcaccgtga acggccacta     780 cttcaagtgc gagggcgagg gcgacggcaa ccccttcgcc ggcacccaga gcatgcggat     840
ccacgtgacc gagggcgccc cctgcccctt cgccttcgac atcctggccc ctgctgcga     900 gtacggcagc aggaccttcg tgcaccacac cgccgagatc cccgacttct tcaagcagag     960
cttccccgag ggcttcacct gggagagaac caccacctac gaggacggcg gcatcctgac    1020
cgcccaccag gacaccagcc tggagggcaa ctgcctgatc tacaaggtga aggtgctggg    1080
caccaacttc cccgccgacg gccccgtgat gaagaacaag agcggcggct gggagcccag    1140
caccgaggtg gtgtaccccg agaacggcgt gctgtgcggc cggaacgtga tggccctgaa    1200
ggtgggcgac cggcggctga tctgccacca ctacaccagc taccgagca agaaggccgt    1260 gcgggccctg accatgcccg gcttccactt caccgacatc cggctgcaga tgctgcggaa    1320

```
ggagaaggac gagtacttcg agctgtacga ggccagcgtg gcccggtaca gcgacctgcc   1380
cgagaaggcc aactga                                                   1396
```

<210> SEQ ID NO 16
<211> LENGTH: 460
<212> TYPE: PRT
<213> ORGANISM: Artificial Sequence
<220> FEATURE:
<223> OTHER INFORMATION: fusion construct

<400> SEQUENCE: 16

```
Met Val Ser Gly Leu Leu Lys Glu Ser Met Arg Ile Lys Met Tyr Met
  1               5                  10                  15

Glu Gly Thr Val Asn Gly His Tyr Phe Lys Cys Glu Gly Glu Gly Asp
             20                  25                  30

Gly Asn Pro Phe Ala Gly Thr Gln Ser Met Arg Ile His Val Thr Glu
         35                  40                  45

Gly Ala Pro Leu Pro Phe Ala Phe Asp Ile Leu Ala Pro Cys Cys Glu
     50                  55                  60

Tyr Gly Ser Arg Thr Phe Val His His Thr Ala Glu Ile Pro Asp Phe
 65                  70                  75                  80

Phe Lys Gln Ser Phe Pro Glu Gly Phe Thr Trp Glu Arg Thr Thr Thr
                 85                  90                  95

Tyr Glu Asp Gly Gly Ile Leu Thr Ala His Gln Asp Thr Ser Leu Glu
            100                 105                 110

Gly Asn Cys Leu Ile Tyr Lys Val Lys Val Leu Gly Thr Asn Phe Pro
        115                 120                 125

Ala Asp Gly Pro Val Met Lys Asn Lys Ser Gly Gly Trp Glu Pro Ser
    130                 135                 140

Thr Glu Val Val Tyr Pro Glu Asn Gly Val Leu Cys Gly Arg Asn Val
145                 150                 155                 160

Met Ala Leu Lys Val Gly Asp Arg Arg Leu Ile Cys His His Tyr Thr
                165                 170                 175

Ser Tyr Arg Ser Lys Lys Ala Val Arg Ala Leu Thr Met Pro Gly Phe
            180                 185                 190

His Phe Thr Asp Ile Arg Leu Gln Met Leu Arg Lys Glu Lys Asp Glu
        195                 200                 205

Tyr Phe Glu Leu Tyr Glu Ala Ser Val Ala Arg Tyr Ser Asp Leu Pro
    210                 215                 220

Glu Lys Ala Asn Arg Ser Pro Gly Met Val Ser Gly Leu Leu Lys Glu
225                 230                 235                 240

Ser Met Arg Ile Lys Met Tyr Met Glu Gly Thr Val Asn Gly His Tyr
                245                 250                 255

Phe Lys Cys Glu Gly Glu Gly Asp Gly Asn Pro Phe Ala Gly Thr Gln
            260                 265                 270

Ser Met Arg Ile His Val Thr Glu Gly Ala Pro Leu Pro Phe Ala Phe
        275                 280                 285

Asp Ile Leu Ala Pro Cys Cys Glu Tyr Gly Ser Arg Thr Phe Val His
    290                 295                 300

His Thr Ala Glu Ile Pro Asp Phe Phe Lys Gln Ser Phe Pro Glu Gly
305                 310                 315                 320

Phe Thr Trp Glu Arg Thr Thr Thr Tyr Glu Asp Gly Gly Ile Leu Thr
                325                 330                 335

Ala His Gln Asp Thr Ser Leu Glu Gly Asn Cys Leu Ile Tyr Lys Val
            340                 345                 350
```

| | | | | | | | | | | |
|---|---|---|---|---|---|---|---|---|---|---|
|Lys|Val|Leu|Gly|Thr|Asn|Phe|Pro|Ala|Asp|Gly|Pro|Val|Met|Lys|Asn|
| | |355| | | |360| | | |365| | | | | |

Lys Ser Gly Gly Trp Glu Pro Ser Thr Glu Val Val Tyr Pro Glu Asn
    370             375             380

Gly Val Leu Cys Gly Arg Asn Val Met Ala Leu Lys Val Gly Asp Arg
385             390             395             400

Arg Leu Ile Cys His His Tyr Thr Ser Tyr Arg Ser Lys Lys Ala Val
        405             410             415

Arg Ala Leu Thr Met Pro Gly Phe His Phe Thr Asp Ile Arg Leu Gln
            420             425             430

Met Leu Arg Lys Glu Lys Asp Glu Tyr Phe Glu Leu Tyr Glu Ala Ser
    435             440             445

Val Ala Arg Tyr Ser Asp Leu Pro Glu Lys Ala Asn
    450             455             460

<210> SEQ ID NO 17
<211> LENGTH: 1424
<212> TYPE: DNA
<213> ORGANISM: Artificial Sequence
<220> FEATURE:
<223> OTHER INFORMATION: fusion construct

<400> SEQUENCE: 17

```
accggtcgcc accatggtga gcggcctgct gaaggagagc atgcgcatca agatgtacat     60
ggagggcacc gtgaacggcc actacttcaa gtgcgagggc gagggcgacg gcaaccccct    120
cgccggcacc cagagcatgc ggatccacgt gaccgagggc gccccctgc ccttcgcctt     180
cgacatcctg gcccctgct gcgagtacgg cagcaggacc ttcgtgcacc acaccgccga    240
gatccccgac ttcttcaagc agagcttccc cgagggcttc acctgggaga gaccaccac    300
ctacgaggac ggcggcatcc tgaccgccca ccaggacacc agcctggagg caactgcct    360
gatctacaag gtgaaggtgc tgggcaccaa cttccccgcc gacggccccg tgatgaagaa    420
caagagcggc ggctgggagc ccagcaccga ggtggtgtac cccgagaacg cgtgctgtg    480
cggccggaac gtgatggccc tgaaggtggg cgaccggcgg ctgatctgcc accactacac    540
cagctaccgg agcaagaagg ccgtgcgggc cctgaccatg cccggcttcc acttcaccga    600
catccggctg cagatgctgc ggaaggagaa ggacgagtac ttcgagctgt acgaggccag    660
cgtggcccgg tacagcgacc tgcccgagaa ggccaacaga tctcccggga tggtgagcgg    720
cctgctgaag gagagcatgc gcatcaagat gtacatggag gcaccgtga acggccacta    780
cttcaagtgc gagggcgagg gcgacggcaa ccccttcgcc ggcacccaga gcatgcggat    840
ccacgtgacc gagggcgccc cctgcccctt cgccttcgac atcctggccc ctgctgcga    900
gtacggcagc aggaccttcg tgcaccacac cgccgagatc cccgacttct tcaagcagag    960
cttccccgag ggcttcacct gggagagaac caccacctac gaggacggcg gcatcctgac   1020
cgcccaccag gacaccagcc tggagggcaa ctgcctgatc tacaaggtga aggtgctggg   1080
caccaacttc cccgccgacg gccccgtgat gaagaacaag agcggcggct gggagcccag   1140
caccgaggtg gtgtaccccg agaacggcgt gctgtgcggc ggaacgtga tggccctgaa   1200
ggtgggcgac cggcggctga tctgccacca ctacaccagc taccggagca agaaggccgt   1260
gcgggccctg accatgcccg gcttccactt caccgacatc cggctgcaga tgctgcggaa   1320
ggagaaggac gagtacttcg agctgtacga ggccagcgtg gcccggtaca gcgacctgcc   1380
cgagaaggcc aacagaactc gagctatgga tgatgatatc gccg                    1424
```

-continued

```
<210> SEQ ID NO 18
<211> LENGTH: 470
<212> TYPE: PRT
<213> ORGANISM: Artificial Sequence
<220> FEATURE:
<223> OTHER INFORMATION: fusion construct

<400> SEQUENCE: 18

Met Val Ser Gly Leu Leu Lys Glu Ser Met Arg Ile Lys Met Tyr Met
 1               5                  10                  15

Glu Gly Thr Val Asn Gly His Tyr Phe Lys Cys Glu Gly Glu Gly Asp
            20                  25                  30

Gly Asn Pro Phe Ala Gly Thr Gln Ser Met Arg Ile His Val Thr Glu
        35                  40                  45

Gly Ala Pro Leu Pro Phe Ala Phe Asp Ile Leu Ala Pro Cys Cys Glu
    50                  55                  60

Tyr Gly Ser Arg Thr Phe Val His His Thr Ala Glu Ile Pro Asp Phe
65                  70                  75                  80

Phe Lys Gln Ser Phe Pro Glu Gly Phe Thr Trp Glu Arg Thr Thr Thr
                85                  90                  95

Tyr Glu Asp Gly Gly Ile Leu Thr Ala His Gln Asp Thr Ser Leu Glu
            100                 105                 110

Gly Asn Cys Leu Ile Tyr Lys Val Lys Val Leu Gly Thr Asn Phe Pro
        115                 120                 125

Ala Asp Gly Pro Val Met Lys Asn Lys Ser Gly Gly Trp Glu Pro Ser
    130                 135                 140

Thr Glu Val Val Tyr Pro Glu Asn Gly Val Leu Cys Gly Arg Asn Val
145                 150                 155                 160

Met Ala Leu Lys Val Gly Asp Arg Arg Leu Ile Cys His His Tyr Thr
                165                 170                 175

Ser Tyr Arg Ser Lys Lys Ala Val Arg Ala Leu Thr Met Pro Gly Phe
            180                 185                 190

His Phe Thr Asp Ile Arg Leu Gln Met Leu Arg Lys Glu Lys Asp Glu
        195                 200                 205

Tyr Phe Glu Leu Tyr Glu Ala Ser Val Ala Arg Tyr Ser Asp Leu Pro
    210                 215                 220

Glu Lys Ala Asn Arg Ser Pro Gly Met Val Ser Gly Leu Leu Lys Glu
225                 230                 235                 240

Ser Met Arg Ile Lys Met Tyr Met Glu Gly Thr Val Asn Gly His Tyr
                245                 250                 255

Phe Lys Cys Glu Gly Glu Gly Asp Gly Asn Pro Phe Ala Gly Thr Gln
            260                 265                 270

Ser Met Arg Ile His Val Thr Glu Gly Ala Pro Leu Pro Phe Ala Phe
        275                 280                 285

Asp Ile Leu Ala Pro Cys Cys Glu Tyr Gly Ser Arg Thr Phe Val His
    290                 295                 300

His Thr Ala Glu Ile Pro Asp Phe Phe Lys Gln Ser Phe Pro Glu Gly
305                 310                 315                 320

Phe Thr Trp Glu Arg Thr Thr Thr Tyr Glu Asp Gly Gly Ile Leu Thr
                325                 330                 335

Ala His Gln Asp Thr Ser Leu Glu Gly Asn Cys Leu Ile Tyr Lys Val
            340                 345                 350

Lys Val Leu Gly Thr Asn Phe Pro Ala Asp Gly Pro Val Met Lys Asn
        355                 360                 365
```

```
Lys Ser Gly Gly Trp Glu Pro Ser Thr Glu Val Val Tyr Pro Glu Asn
    370                 375                 380

Gly Val Leu Cys Gly Arg Asn Val Met Ala Leu Lys Val Gly Asp Arg
385                 390                 395                 400

Arg Leu Ile Cys His His Tyr Thr Ser Tyr Arg Ser Lys Lys Ala Val
                405                 410                 415

Arg Ala Leu Thr Met Pro Gly Phe His Phe Thr Asp Ile Arg Leu Gln
                420                 425                 430

Met Leu Arg Lys Glu Lys Asp Glu Tyr Phe Glu Leu Tyr Glu Ala Ser
            435                 440                 445

Val Ala Arg Tyr Ser Asp Leu Pro Glu Lys Ala Asn Arg Thr Arg Ala
    450                 455                 460

Met Asp Asp Asp Ile Ala
465                 470

<210> SEQ ID NO 19
<211> LENGTH: 27
<212> TYPE: DNA
<213> ORGANISM: Artificial Sequence
<220> FEATURE:
<223> OTHER INFORMATION: primer

<400> SEQUENCE: 19
acatggatcc gctggtttgt tgaaaga                                        27

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
acctcagtgc ttggctccca t                                             21

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
atgggagcca agcactgagg t                                             21

<210> SEQ ID NO 22
<211> LENGTH: 32
<212> TYPE: DNA
<213> ORGANISM: Artificial Sequence
<220> FEATURE:
<223> OTHER INFORMATION: primer

<400> SEQUENCE: 22
tgacaagctt ctggtgtcac tgggaacaat ca                                 32

<210> SEQ ID NO 23
<211> LENGTH: 684
<212> TYPE: DNA
<213> ORGANISM: heteractis crispa
```

<400> SEQUENCE: 23

```
atggctggtt tgttgaaaga agtatgcgc atcaagatgt acatggaagg cacggttaat    60
ggccattatt tcaagtgtga aggagaggga cacggcaacc catttacagg tacgcagagc   120
atgaggattc atgtcaccga aggggctcca ttaccatttg ccttcgacat tttggcaccg   180
tgttgtgagt acggcagcag gacctttgtc caccatacgg cagagattcc cgatttcttc   240
aagcagtctt tccctgaagg ctttacttgg aaagaaccca caacctatga agatggaggc   300
attcttactg ctcatcagga cacaagcctg gagggaact gccttatata caaggtgaaa   360
gtccttggta ccaattttcc tgctgatggc cccgtgatga gaacaaatc aggaggatgg   420
gagccaagca ctgaggtggt ttatccagag aatggtgtcc tgtgtggacg taatgtgatg   480
gcccttaaag tcggtgatcg tcgtttgatc tgccatctct atacttctta caggtccaag   540
aaagcagtcc gtgccttgac aatgccagga tttcatttta cagacatccg ccttcagatg   600
ccgaggaaaa agaagacga gtactttgaa ctgtacgaag catctgtggc taggtacagt   660
gatcttcctg aaaaagcaaa ttga                                          684
```

<210> SEQ ID NO 24
<211> LENGTH: 227
<212> TYPE: PRT
<213> ORGANISM: heteractis crispa

<400> SEQUENCE: 24

```
Met Ala Gly Leu Leu Lys Glu Ser Met Arg Ile Lys Met Tyr Met Glu
  1               5                  10                  15
Gly Thr Val Asn Gly His Tyr Phe Lys Cys Glu Gly Glu Gly Asp Gly
                 20                  25                  30
Asn Pro Phe Thr Gly Thr Gln Ser Met Arg Ile His Val Thr Glu Gly
             35                  40                  45
Ala Pro Leu Pro Phe Ala Phe Asp Ile Leu Ala Pro Cys Cys Glu Tyr
         50                  55                  60
Gly Ser Arg Thr Phe Val His His Thr Ala Glu Ile Pro Asp Phe Phe
 65                  70                  75                  80
Lys Gln Ser Phe Pro Glu Gly Phe Thr Trp Glu Arg Thr Thr Thr Tyr
                 85                  90                  95
Glu Asp Gly Gly Ile Leu Thr Ala His Gln Asp Thr Ser Leu Glu Gly
                100                 105                 110
Asn Cys Leu Ile Tyr Lys Val Lys Val Leu Gly Thr Asn Phe Pro Ala
            115                 120                 125
Asp Gly Pro Val Met Lys Asn Lys Ser Gly Gly Trp Glu Pro Ser Thr
        130                 135                 140
Glu Val Val Tyr Pro Glu Asn Gly Val Leu Cys Gly Arg Asn Val Met
145                 150                 155                 160
Ala Leu Lys Val Gly Asp Arg Arg Leu Ile Cys His Leu Tyr Thr Ser
                165                 170                 175
Tyr Arg Ser Lys Lys Ala Val Arg Ala Leu Thr Met Pro Gly Phe His
            180                 185                 190
Phe Thr Asp Ile Arg Leu Gln Met Pro Arg Lys Lys Asp Glu Tyr
        195                 200                 205
Phe Glu Leu Tyr Glu Ala Ser Val Ala Arg Tyr Ser Asp Leu Pro Glu
    210                 215                 220
Lys Ala Asn
225
```

<210> SEQ ID NO 25
<211> LENGTH: 680
<212> TYPE: DNA
<213> ORGANISM: heteractis crispa

<400> SEQUENCE: 25

```
tctggtttgt tgaaagaaag tatgcgcatc aagatgtaca tggaaggcac ggttaatggc      60
cattatttca agtgtgaagg agagggagac ggcaacccat ttgcaggtac gcagagcatg     120
aggattcatg tcaccgaagg ggctccatta ccatttgcct cgacatttt  ggcaccgtgt     180
tgtgcgtacg gcagcaggac ctttgtccac catacggcag agattcccga tttcttcaag     240
cagtctttcc ctgaaggctt tacttgggaa agaaccacaa cctatgaaga tggaggcatt     300
cttactgctc atcaggacac aagcctggag gggaactgcc ttatatacaa ggtgaaagtc     360
cttggtacca attttcctgc tgatggcccc gtgatgaaga aaaatcagga ggatgggagc     420
caagcactga ggtggtttat ccagagaatg gtgtcctgtg tggacgtaat gtgatggccc     480
ttaaagtcgg tgatcgtcgt tgatctgcca atcactatac ttcttacagg tccaagaaag     540
cagtccgtgc cttgacaatg ccaggatttc attttacaga catccgcctt cagatgctga     600
ggaaaaagaa agacgagtac tttgaactgt acgaagcatc tgtggctagg tacagtgatc     660
ttcctgaaaa agcaaattga                                                 680
```

<210> SEQ ID NO 26
<211> LENGTH: 226
<212> TYPE: PRT
<213> ORGANISM: heteractis crispa

<400> SEQUENCE: 26

```
Ser Gly Leu Leu Lys Glu Ser Met Arg Ile Lys Met Tyr Met Glu Gly
  1               5                  10                  15
Thr Val Asn Gly His Tyr Phe Lys Cys Glu Gly Glu Gly Asp Gly Asn
             20                  25                  30
Pro Phe Ala Gly Thr Gln Ser Met Arg Ile His Val Thr Glu Gly Ala
         35                  40                  45
Pro Leu Pro Phe Ala Phe Asp Ile Leu Ala Pro Cys Cys Ala Tyr Gly
     50                  55                  60
Ser Arg Thr Phe Val His His Thr Ala Glu Ile Pro Asp Phe Phe Lys
 65                  70                  75                  80
Gln Ser Phe Pro Glu Gly Phe Thr Trp Glu Arg Thr Thr Thr Tyr Glu
                 85                  90                  95
Asp Gly Gly Ile Leu Thr Ala His Gln Asp Thr Ser Leu Glu Gly Asn
            100                 105                 110
Cys Leu Ile Tyr Lys Val Lys Val Leu Gly Thr Asn Phe Pro Ala Asp
        115                 120                 125
Gly Pro Val Met Lys Asn Lys Ser Gly Gly Trp Glu Pro Ser Thr Glu
    130                 135                 140
Val Val Tyr Pro Glu Asn Gly Val Leu Cys Gly Arg Asn Val Met Ala
145                 150                 155                 160
Leu Lys Val Gly Asp Arg Arg Leu Ile Cys His His Tyr Thr Ser Tyr
                165                 170                 175
Arg Ser Lys Lys Ala Val Arg Ala Leu Thr Met Pro Gly Phe His Phe
            180                 185                 190
Thr Asp Ile Arg Leu Gln Met Leu Arg Lys Lys Asp Glu Tyr Phe
        195                 200                 205
```

```
                                          -continued
Glu Leu Tyr Glu Ala Ser Val Ala Arg Tyr Ser Asp Leu Pro Glu Lys
    210                 215                 220
Ala Asn
225
```